United States Patent
Palinski et al.

(10) Patent No.: US 8,961,982 B2
(45) Date of Patent: Feb. 24, 2015

(54) MODULATION OF DEVELOPMENTAL IMMUNE PROGRAMMING AND PROTECTION AGAINST CARDIOVASCULAR DISEASE, DIABETES, INFECTIOUS DISEASES, AND CANCER

(75) Inventors: Wulf Palinski, San Diego, CA (US); Tomoya Yamashita, Kobe (JP)

(73) Assignee: The Regents of the University of California, Oakland, CA (US)

( * ) Notice: Subject to any disclaimer, the term of this patent is extended or adjusted under 35 U.S.C. 154(b) by 1367 days.

(21) Appl. No.: 12/139,053

(22) Filed: Jun. 13, 2008

(65) Prior Publication Data

US 2008/0311152 A1 Dec. 18, 2008

Related U.S. Application Data

(63) Continuation-in-part of application No. PCT/US2006/047458, filed on Dec. 12, 2006.

(60) Provisional application No. 60/977,697, filed on Oct. 5, 2007, provisional application No. 60/751,029, filed on Dec. 16, 2005.

(51) Int. Cl.
*A61K 39/00* (2006.01)

(52) U.S. Cl.
CPC ......... *A61K 39/0012* (2013.01); *A61K 39/0008* (2013.01); *A61K 2039/55* (2013.01); *A61K 2039/6081* (2013.01)
USPC .................. 424/184.1; 424/185.1; 424/193.1; 514/1.9; 514/6.9; 514/16.4

(58) Field of Classification Search
None
See application file for complete search history.

(56) References Cited

U.S. PATENT DOCUMENTS

| 6,825,318 | B2 | 11/2004 | Kim et al. |
| 6,838,452 | B2 * | 1/2005 | Harats et al. .................. 514/114 |
| 7,090,855 | B1 * | 8/2006 | Hyoty et al. ............... 424/217.1 |
| 2003/0064915 | A1 | 4/2003 | Strominger et al. |
| 2003/0114367 | A1 * | 6/2003 | Shoenfeld et al. ............. 514/12 |

FOREIGN PATENT DOCUMENTS

WO    WO 0100236 A1 *   1/2001

OTHER PUBLICATIONS

Victor et al., J Allergy Clin Immunol, 2003, 111:269-277.*
Palinski et al., FASEB J., 2002, 16:1348-1360.*
Standl E., Clin. Invest Med., 1995, 18:261-266.*
Merck Manual of Diagnosis and Therapy, $17^{th}$ edition, editors Beers and Berkow, 1999, pp. 1097-1101.*

(Continued)

*Primary Examiner* — Michael Szperka
(74) *Attorney, Agent, or Firm* — Joseph R. Baker, Jr.; Gavrilovich, Dodd & Lindsey LLP

(57) ABSTRACT

Maternal adaptive immunity conveys temporary humoral immune protection to neonates. The disclosure demonstrates the influence of the in utero environment on adult atherosclerosis and provides evidence for persistent effects of maternal immunization on adult immune responses. The disclosure provides methods and compositions useful for immunization and more particularly for actively modulating the fetal programming of the immune system for the purpose of preventing or treating immune-modulated diseases. The disclosure also provides interventions to protect offspring and immunized subjects against insulin resistance.

18 Claims, 10 Drawing Sheets

(56) References Cited

OTHER PUBLICATIONS

Rahman et al., Bulletin of the World Health Organization, 1982, 60:261-267.*
Koenig et al., Am J Public Health, 1998, 88:903-907.*
Ramagopalan et al., Lancet, 2010, 9:727-739.*
Wilson et al., Braz J Infect Dis, 2009, 13:304-310.*
Janeway et al., Immunobiology, 3rd edition, 1997, Garland Publications, pp. 8:1-8:17.*
Palinski et al., Journal of Internal Medicine, 2000, 247:371-380.*
Quinello et al., Scand J Immunol. Jul. 2010;72(1):66-73. doi: 10.1111/j.1365-3083.2010.02410.x.*
Download from world wide web .who.int/topics/breastfeeding/en/ on Jul. 7, 2014.*
Polte et al., Clin Exp Allergy. Dec. 2008;38(12):1950-8. doi: 10.1111/j.1365-2222.2008.03096.x. Epub Sep. 4, 2008.*
Zinkernagel, R., Expert Rev Vaccines. Jul. 2014;13(7):821-3. doi: 10.1586/14760584.2014.924402. Epub Jun. 7, 2014.*
Bergerot et al. "A cholera toxoid-insulin conjugate as an oral vaccine against spontaneous autoimmune diabetes," Proc. Natl. Acad. Sci. USA, Apr. 1997, pp. 4610-4614, vol. 94.
Melkild et al., "Maternal allergen immunization during pregnancy in a mouse model reduces adult allergy-related antibody responses in the offspring," Clinical and Experimental Allergy, Sep. 2002, pp. 1370-1376, vol. 32, No. 9.
Palinski et al., "Immunization of low density lipoprotein (LDL) receptor-deficient rabbits with homologous malondialdyhyde-modified LDL reduces atherogenesis," Proc. Natl. Acad. Sci. USA, Jan. 1995, pp. 821-825, vol. 92.
Notification Concerning Transmittal of International Preliminary Report on Patentability (Chapter I of the Patent Cooperation Treaty), Jun. 18, 2008.

* cited by examiner

MODULATION OF DEVELOPMENTAL IMMUNE PROGRAMMING AND PROTECTION AGAINST CARDIOVASCULAR DISEASE, DIABETES, INFECTIOUS DISEASES, AND CANCER

CROSS REFERENCE TO RELATED APPLICATIONS

The application claims priority as a continuation-in-part to International Application No. PCT/US2006/047458 filed Dec. 12, 2006, which claims priority under 35 U.S.C. §119 to U.S. Provisional Application Ser. No. 60/751,029, filed Dec. 16, 2005, and this application claims priority to U.S. Provisional Application No. 60/977,697, filed Oct. 5, 2007, the disclosures of which are incorporated herein by reference.

STATEMENT REGARDING FEDERALLY SPONSORED RESEARCH

This invention was made with government support under HL56989 and HL67792 awarded by National Institutes of Health. The government has certain rights in the invention.

TECHNICAL FIELD

This invention relates to the field of therapeutic methods, compositions and uses thereof, in the treatment of infectious and autologous diseases and disorders in mammalian subjects. More particularly the disclosure relates to developmental programming via maternal exposure.

BACKGROUND

Although it is tempting to assume that the passing-on of maternal immune memory would convey an evolutionary advantage, the only well established mechanism consists of the temporary protection of neonates by maternal IgG antibodies carried across the placenta, or, in animals but not humans, antibody coating of enterocyte surfaces during lactation (Zinkernagel, R. M., Maternal antibodies, childhood infections, and autoimmune diseases. N. Engl. J. Med. 345, 1331-1335 (2001)). All other active humoral immune defenses are thought to depend on mature B and T cells and to require "learning", i.e. clonal expansion of antigen-specific lymphocytes (Abbas et al., Cellular and Molecular Immunology (Elsevier, 2005); Germain, Nat. Med. 10: 1307-20 (2004)), with the possible exception of B-1 cell derived natural IgM antibodies that convey protection against a limited repertoire of bacterial antigens (Kantor et al., J. Immunol. 158, 1175-1186 (1997); Hayakawa et al. Science 285, 113-116 (1999)).

SUMMARY

The disclosure demonstrates the unexpected existence of a mechanism through which maternal immune memory may influence active immune responses and susceptibility to immune-modulated diseases in their offspring.

The disclosure provides a method of fetal immune programming comprising administering an antigen, which induces an immune response, to a maternal subject carrying a fetus, whereby the immune response induces immune programming in the fetus. The method can further comprise administering an antigen or immunostimulatory agent (e.g., a cytokine or adjuvant) to the offspring of the maternal subject thus treated, after birth, whereby the immune responses programmed in utero are enhanced.

The disclosure also provides a method of fetal immune programming comprising administering an antigen or immunostimulatory agent, which induces an immune response, to a female subject, wherein the immune response in the female subject induces fetal immune programming when she becomes pregnant at a later time.

The disclosure provides a method of immunization of a postnatal subject, comprising administering an antigen, which induces an immune response, to a maternal subject prior to pregnancy or while carrying a fetus or expecting to become pregnant, wherein the immune response induces immune programming in the fetus and life-long changes in the postnatal subject's immune system that protect against a disease or disorder. In one aspect, the process results in the increase in IgG and IgM antibodies to the antigen and memory cells in the unborn fetus during gestation and into adult hood.

The disclosure further provides a method of fetal immune programming comprising administering an antigen, which induces an immune response, to a female subject, wherein the immune response in the female subject induces fetal immune programming during a pregnancy by increaseing IgM and IgG antibodies to an antigen found in a child born to the mother.

The disclosure also provides a method for treating or preventing an autoimmune disorder in a neonatal subject having or at risk of acquiring the disorder, comprising administering to a maternal subject an immunomodulatory effective amount of at least one epitope from a self-antigen in a pharmaceutically acceptable carrier, wherein the epitope provides a regulatory immune response in the maternal subject and wherein the immune response induces immune programming in a fetus and life-long changes in the neonatal subject's immune system.

The disclosure provides a method of inducing protective immunity in a neonate subject comprising administering a composition that induces an immune response in a subject, wherein the composition is administered to a maternal subject prior to and/or during pregnancy with the neonate subject.

In certain methods of the disclosure the antigen comprises allogeneic antigens obtained from donors suffering from an immune-related or immune-mediated disorder or disease, xenogenic antigens, syngeneic antigens, autologous antigens, non-autologous antigens, recombinantly prepared antigens, or any combination thereof. The antigens can be a viral antigen, a bacterial antigen, a parasitic antigen, an antigen that induces autoimmune disease, or an autologous antigen. In other aspect, the method of administration comprises oral, intravenous, parenteral, transdermal, subcutaneous, intravaginal, intraperitoneal, intranasal, mucosal, sublingual, topical or rectal administration, or any combination thereof. In a specific embodiment, the antigen comprises LDL, peptides of apolipoprotein B-100, phospholipid components of LDL, HDL, VLDL, IDL and LP(a). The antigen can comprise an oxidative neoepitope. In one aspect, the antigen is not an allergen. In another aspect, the antigen does not alter IgE antibody production in the immunized mother or her child specific to the allergen used to immunize the mother or other allergens.

Using the methods and compositions of the disclosure, a number of disease and disorder can be treated, including atherosclerosis, obesity, insulin resistance, non insulin dependent diabetes mellitus (NIDDM), and insulin dependent diabetes mellitus (IDDM). Other diseases and disorders include multiple sclerosis (MS), rheumatoid arthritis, lupus erythematosus, IDDM, scleroderma, myasthenia gravis and ulcerative colitis. Some of the interventions described above may, in addition to protecting offspring against the conditions listed, delay or prevent the onset of insulin resistance in the maternal subject, or male subjects subjected to the same treatment.

The details of one or more embodiments are set forth in the accompanying drawings and the description below. Other features, objects, and advantages will be apparent from the description and drawings, and from the claims.

DETAILED DESCRIPTION

Figure 1:
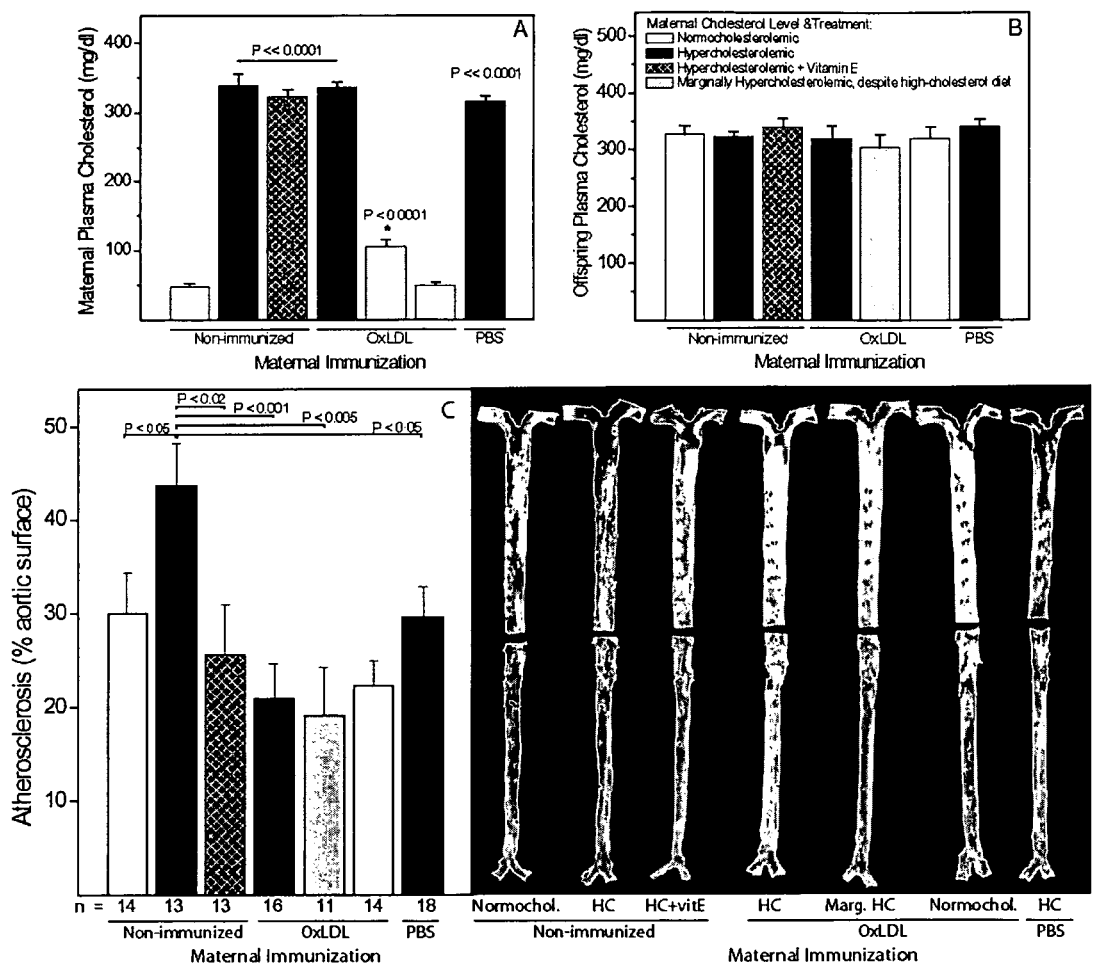
FIG. 1A-C show maternal immunization reduces aortic atherosclerosis in offspring. (A) Maternal total plasma cholesterol levels. Data are mean±SEM. (B) Time-averaged total cholesterol level of offspring during the 5 months of dietary intervention. (C) Atherosclerosis in 6 months old offspring. Left: Percentage of aortic surface area covered by atherosclerotic lesions determined by computer-assisted image analysis. Maternal immunization and animal numbers are indicated in the abscissa. Maternal immunization and subsequent cholesterol levels/vitamin E treatment during pregnancy are indicated in the legend. Right: Representative Sudan-stained aortas.

As used herein and in the appended claims, the singular forms "a," "and," and "the" include plural referents unless the context clearly dictates otherwise. Thus, for example, reference to "an antigen" includes a plurality of such antigens and reference to "the immune cell" includes reference to one or more immune cells known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Maternal adaptive immunity conveys temporary humoral immune protection to neonates, but little is known about its influence on fetal differentiation of B and T cells and innate or adaptive immune responses later in life. The in utero environment is an important determinant of postnatal disease. In particular, a wealth of epidemiological evidence links dysmetabolic conditions during pregnancy with atherosclerosis, diabetes, and hypertension later in life. The increasing prevalence of maternal hypercholesterolemia, insulin resistance (IR) and diabetes is therefore expected to lead to a wave of cardiovascular disease in their offspring.

It should be understood that allergen desensitization is a process the seeks to reduce the amounts of reactive IgE antibodies produced or circulating in a subject that can react with an allergen. In other words, delivery of an allergen to a subject repeatedly results in a decrease in IgE production in a subject, or an offspring. This is contrasted with immune programming that seeks to develop memory cells capable of identifying and responding (i.e., producing an immune response) to an antigen. Furthermore, it is recognized that IgG antibodies are capable of being delivered to a fetal subject through the mother's milk and across the placenta, however, such "crossing" of IgG antibodies is a transient process and should not be confused with immune programming, which is directed to the development of active immune responses, i.e. immune cells within a subject capable of recognizing an antigen and producing a response that is "self" produced and life-long. In another aspect, the immune programming leads to protective responses, such as increased IgM and IgG antibodies against antigens that promote disease, as opposed to IgE that cause detrimental (allergic) effects. Antigens that promote disease can include auto-immune antigens, inflammatory (non-allergic) disease antigens and infectious antigens.

Insulin resistance (IR) is associated with several disease conditions including non-insulin dependent diabetes mellitus (NIDDM), obesity, hypertension, and cardiovascular disease. The most well-studied of these conditions is NIDDM. NIDDM, also termed maturity-onset diabetes or type II diabetes to differentiate it from insulin-dependent diabetes mellitus (IDDM, also termed type I or juvenile diabetes), usually occurs in middle-aged obese people and accounts for 80% to 90% of diagnosed diabetes. In addition to insulin resistance, NIDDM is associated with hyperglycemia, increased levels of very low density lipoproteins (VLDL), and decreased muscle uptake of glucose. Apart from being associated with clinically manifest NIDDM, insulin resistance is associated with obesity and the metabolic syndrome, and is considered a precursor and potential cause of NIDDM.

During the past decade it has been established that maternal hypercholesterolemia is one of the causes of developmental programming of atherosclerosis. Maternal hypercholesterolemia during pregnancy, even if only temporary, is associated with markedly increased fatty streak formation in human fetal arteries and accelerated progression of atherosclerosis during normocholesterolemic childhood. Dietary studies in genetically more homogeneous animal models have established the causal role of maternal hypercholesterolemia and the ensuing increased oxidative stress. Studies in mice have also shown persistent effects of maternal hypercholesterolemia on arterial gene and protein expression in their offspring. Most importantly, cholesterol-lowering and antioxidant treatment of mothers during pregnancy markedly reduced postnatal atherogenesis, indicating that long-term benefits can be achieved by protecting against atherogenic in utero programming.

The role of inflammation in atherogenesis is well established. Hypercholesterolemia and increased lipid peroxidation enhance inflammation by interfering with several oxidation-sensitive nuclear signaling pathways that influence arterial leukocyte recruitment and secretory activity, such as the NFκB and PPAR pathways. Diabetes and the metabolic syndrome also promote inflammation, and conversely, PPAR-agonists administered to insulin-resistant mice decrease inflammation and atherogenesis. Although many immune mechanisms are proinflammatory and proatherogenic, others are protective. For example, immunization of adult experimental animals with oxidized LDL (OxLDL), an antigen accumulating in atherosclerotic lesions, markedly inhibits atherogenesis. Furthermore, as the disclosure demonstrates, vaccination with OxLDL also reduces the risk of insulin resistance.

A study investigating the role of the in utero environment on adult atherosclerosis provided evidence for persistent effects of maternal immunity on adult immune responses and atherogenesis. Maternal hypercholesterolemia during pregnancy enhances the onset of the disease in the fetal aorta and accelerates postnatal atherogenesis in humans and experimental models. In adults, hypercholesterolemia increases lipid peroxidation and formation of oxidized LDL (OxLDL), which triggers humoral and cellular immune responses. Although pro-inflammatory immune mechanisms generally enhance atherosclerosis, immunizations with OxLDL reduce its progression in the immunized subjects. The disclosure provides evidence that similar immunization of the prospective mother also benefits her offspring, both by protecting the fetus against atherogenic programming by maternal hypercholesterolemia and by programming postnatal immune responses. The disclosure shows that maternal immunization markedly reduced atherosclerosis not only in offspring of hypercholesterolemic mothers, but also in offspring of normocholesterolemic mothers. It also describes postnatal immune responses that were programmed in utero. For example, naïve offspring of immunized mothers showed persistent increases in circulating IgM-LDL immune complexes, as well as significantly greater titers of IgG and IgM antibodies against oxidation-specific epitopes in response to immune challenge with OxLDL.

The disclosure provides methods and compositions used for inducing maternal adaptive immunity resulting in enhanced immune responses in their offspring through fetal programming. The disclosure also shows that postnatal exposure of offspring to spontaneously formed or naturally encountered antigens, or one-time administration of the antigen to of naïve offspring, enhances the programmed immune responses after birth. As demonstrated, in principle, for atherosclerosis, fetal immune programming constitutes a way to reduce immune-modulated adult diseases.

The disclosure provides methods for maternal immunization with antigens that are immunologically similar to antigens formed in vivo, or present in pathogens, such that the antigens influence the immune system of the offspring of the maternal subject beyond the neonatal period and into youth and/or adult age. In one aspect, the immunization of the maternal subject increases formation of IgM antibodies or immune complexes of such IgM with their respective antigen, and increases IgM and IgG immune responses to antigen challenge in their offspring.

It is important to understand that the methods and compositions described herein provide a distinctive advantage over well established passive immunoprotection of neonates by maternal IgG antibodies crossing the placenta, which lasts only for a limited postnatal period. In contrast, immunization of the mother offers long-term immune protection by influencing active immune defenses in the offspring. The acquired (adaptive) immunity of the maternal subject influences the differentiation of B and T lymphocytes during fetal development (i.e., immune programming). Thus, the disclosure provides methods and compositions for using the mother's immune system to provide their offspring a life-long advantage by priming their immune system in a way—or ways— that protect against acute or chronic conditions. Accordingly, (i) it is possible to enhance postnatal immune responses by non-specific immune-stimulation of the mother; (ii) it is possible by such generic stimulation to prime offspring immune responses not just to one particular maternal antigen, but to a whole repertoire of antigens to which she has acquire immunity; and (iii) the identification of the mechanisms leading to immune programming provides for the development of novel therapeutic approaches to enhance offspring immunity (e.g. targeting particular cell subsets or specific interleukins).

The compounds, compositions, and methods of the disclosure may also be used to induce tolerance to various autoantigens in neonates and infants. More particularly, the disclosure further provides compositions and methods for conferring resistance in neonate or infant mammals to the induction of an autoimmune disease during adult life through a process of fetal programming.

The methods and compositions of the disclosure are useful in protecting offspring by maternal immunization. The advantages are readily apparent in that there would be reduced mortality and morbidity due to infectious disease, autoimmune and autologous disease and disorders. Furthermore, the fetal programming would provide advantages to the neo-natal subject throughout life by providing a protective immunity to various infectious agents and disease and disorders having recognizable antigenic determinants.

The disclosure also demonstrates a protective effect of immunizations on insulin-sensitivity, not only in their offspring, but in immunized animals in general. The same therapeutic interventions that modify in utero programming can therefore prevent or delay the onset of insulin resistance and related diabetic conditions in adult subjects of both genders.

"Developmental programming" (used synonymous with "in utero programming" or "fetal programming") is a term describing lifelong changes in function that follow a particular event in an earlier period of the life span of the subject. This should not be confused with passive immunity resulting from transient crossing of IgG antibodies in a mother's milk or during pregnancy. Developmental programming includes the ability to develop an increased immune response to an antigen after birth and weaning from a mother's milk. For example, exposure of a fetus to environmental factors within the womb of the mother can result in persistent changes in function following birth.

Passive immunity refers to the transfer of humoral immunity in the form of antibodies, from one individual to another. Passive immunity occurs when maternal antibodies are transferred to the fetus across the placenta or to neonates through a mother's milk. The antibodies are not produced by the "immunized subject" but are rather obtained or administered from a heterologous individual. The most recognized form of passive immunity is maternal passive immunity. Material passive immunity is an antibody-mediated immunity conveyed to a fetus by its mother during pregnancy. Maternal antibodies are passed to the fetus across the placentas by an FcRn receptor on placental cells. Maternal antibodies passed to a fetus or newborn have a short and limited half-life of approximately 14 days to the first few months, and thus only have an effect the first month of a newborn's life. Another type of passive immunity is artificially acquired passive immunity, a short-term immunization achieved by the transfer of antibodies. Passive immunity provides immediate protection, but the body does not develop memory, therefore the patient is at risk of being infected by the same pathogen later.

In contrast, the methods and compositions of the disclosure provide fetal programming resulting in immunity that extends beyond a newborn's first days or months. For example, the data demonstrates that immunization of a subject prior to or during pregnancy can lead to immunity in the offspring that extends beyond the first month of a newborn's life. Furthermore, the methods and compositions provided herein demonstrate that the maternal subject's offspring develop a memory for the antigen that provides the offspring the ability to rapidly generate antibodies to that particular (or an immunologically similar) antigen.

Accordingly, a non-passive immunity refers to any one or more of (i) the programming of immune cells in a subject such that the immune cells can produce more antibodies to an antigen (e.g., by increasing the number of antigen-specific B-cells); (ii) the generation of memory cells in a subject to an antigen; (iii) an immunity that extends beyond the childhood into juvenile, pre-adult or adult subject's life; (iv) autologous antibodies capable of binding an antigen; and (v) an increased reactivity of a subject's immune system to an antigen.

An "antigen" is a molecule or a portion of a molecule capable of (i) inducing an immune response in a subject exposed to the antigen, and/or (ii) capable of being bound by an antibody. An antigen may have one or more than one epitope. The term "epitope" is meant to refer to that portion of any molecule capable of being recognized by the immune system of a subject and/or capable of being bound by an antibody. An antigen can elicit an immune response when administered to a mammalian subject on its own and/or together with an immune enhancing molecule. An antigen or epitope can comprise a self-antigen or grammatical equivalents thereof from any protein, carbohydrate or other component capable of eliciting an immune response.

As used herein, an "immune enhancing molecule" is a molecule (e.g., a polypeptide) that, when administered to a mammalian subject in the form of a fusion agent or pharmaceutical formulation comprising an antigen and an immune enhancing molecule, elicits a more potent immune response to the antigen molecule than would the antigen molecule administered alone to the mammalian subject. It is understood that the immune enhancing molecule, when administered to the subject can elicit an immune producing response itself.

Immune enhancing molecules include commonly used adjutants. For example, immune enhancing molecules include proteins, carbohydrates, lipids, or nucleic acids. They are typically proteins or functional fragments of such proteins. Examples of such molecules include ESAT-6 and Omps or functional fragments thereof. Methods for establishing whether a given molecule enhances the Th1 response in a subject to a prospective immune enhancing molecule are known to one skilled in the art.

The term "low density lipoprotein" (LDL) refers to the low-density fraction of lipoproteins present in blood plasma. Lipoproteins are the particles that carry water-insoluble long-chain lipids through aqueous blood plasma and are classified according to their density into chylomicrons, very low density lipoproteins (VLDL), LDL and high density lipoproteins (HDL). They consist of a spherical non-polar core containing mainly triglycerides and cholesteryl esters, and a polar (water-soluble) outer membrane composed of phospholipids, apolipoproteins and free cholesterol. LDL is the main carrier of cholesterol taken up into the arterial wall. It has a density-range of 1.006 to 1.063 µg/ml and carries a single apolipoprotein, apoB-100, which consists of approximately 4500 amino acids and contains about 360 free amino residues. Oxidation of lipids in the core of lipoprotein particles leads to the formation of reactive aldehydes and oxidized phospholipids, both of which can react with free amino residues of apoB-100 and other tissue proteins. Modification of amino residues of apoB impairs the recognition of LDL by receptors in the liver, which normally remove LDL from the circulation, and leads to recognition by scavenger receptors of macrophages. Unregulated uptake of OxLDL by scavenger receptors of macrophages in the arterial wall is a key event in the formation of atherosclerotic lesions. Exemplary oxidized phospholipid include oxidized forms of 1-palmitoyl-2-arachidonoyl-sn-glycero-3-phos-phorylcholine (Ox-PAPC), 1-palmitoyl-2-oxovaleroyl-sn-glycero-3-phosphoryl-choline (POVPC), 1-palmitoyl-2-glutaroyl-sn-glycero-3-phosphorylcholine (PGPC), 1-palmitoyl-2-epoxyisoprostane-sn-glycero-3-phosphorylcholine (PEIPC), oxidized 1-stearoyl-2-arachidonoyl-sn-glycero-3-phosphorylcholin-e (Ox-SAPC), 1-stearoyl-2-oxovaleroyl-sn-glycero-3-phosphorylcholine (SOVPC, 1-stearoyl-2-glutaroyl-sn-glycero-3-phosphorylcholine (SGPC), 1-stearoyl-2-epoxyisoprostane-sn-glycero-3-phosphorylcholine (SEIPC), 1-stearoyl-2-arachidonyl-sn-glycero-3-phosphorylethanolamine(Ox-SAPE), 1-stearoyl-2-oxovaleroyl-sn-glycero-3-phosphorylethanolamine(SOVPE), 1-stearoyl-2-glutaroyl-sn-glycero-3-phosphorylethanolamine(SGPE), and 1-stearoyl-2-epoxyisoprostane-sn-glycero-3-phosphorylethanolamine(SEIPE).

OxLDL contains a variety of "oxidation-specific" neoepitopes on both the lipid and protein moieties (Horkko et al., Free Radic. Biol. Med. 28:1771-1779, 2000). For example, reactive decomposition products of phospholipid oxidation, such as 1-palmitoyl-2-(5-oxovaleroyl)-sn-glycero-3-phosphorylcholine (POVPC) can covalently modify protein and lipid moieties of LDL, to form adducts that retain the intact phosphorylcholine (PC) headgroup. Modification with POVPC and other decomposition products resulting from lipid peroxidation, such as malondialdehyde (MDA), leads to formation of "neo-self epitopes" that are recognized by innate and/or adaptive immunity (Palinski et al., Arteriosclerosis 10:325-335, 1990; Palinski et al., J. Clin. Invest. 98:800-814, 1996).

The methods and compositions of the disclosure include the use of any antigen capable of inducing an immune response in a subject. For example, the disclosure includes the use of antigens associated with autoimmune/autologous immune responses, infectious diseases, cell proliferative disorders (e.g., neoplasms and cancer), vascular diseases, diabetes and the like. The methods and compositions of the disclosure contemplate the use of antigens associated with infectious organisms including, but are not limited to, viruses, bacteria, protozoa, fungi, and parasites.

In some embodiments of the disclosure, the subject (e.g., a maternal subject) is administered a series of vaccinations to produce a full, broad immune response. According to one aspect at least two and typically four injections are given over a period of time. The period of time between injections may include from 24 hours apart to two weeks or longer between injections, typically one week apart. Alternatively, at least two and up to four separate injections are given simultaneously at different parts of the body. In another aspect, the maternal individual is subjected to immunization to induce fetal programming during pregnancy, the mother's offspring may typically then be immunized or boosted with the minimizing antigen after birth.

The disclosure generally discusses immunization in the context of prophylactic methods of protection. Thus, a method of immunizing includes methods of protecting an individual from pathogen challenge or occurrence or proliferation of specific cells as well as autoimmune disease (e.g., diabetes).

The methods and compositions of the disclosure are applicable to a wide range of species, e.g., humans, non-human primates, horses, cattle, pigs, sheep, goats, dogs, cats, rabbits, guinea pigs, hamsters, rats, and mice. While the disclosure herein primarily relates to uses of the methods of the disclosure to immunize humans, the methods of the disclosure can be applied to veterinary medical uses too. It is within the scope of the disclosure to provide methods of immunizing non-human as well as human individuals against pathogens, autoimmune disorders and diseases. The disclosure relates to genetic immunization as well as pharmaceutical immunization of mammals (including humans), birds and fish. The methods of the disclosure can be particularly useful for mammalian species including human, bovine, ovine, porcine, equine, canine and feline species.

Autoimmune diseases typically begin with abnormal regulation of autoreactive T cells either due to bystander activation or due to molecular mimicry. For example, a viral infection or exposure to a superantigen may provide sufficient co-stimulation resulting in activation of few low affinity autoreactive T cells that escape the thymus selection process. Abnormal down-regulation of such autoreactive responses may lead to expansion of pathogenic T cells that infiltrate the organ or react with an antigen where the recognized antigen is present. A few host-related factors facilitate the transition between non-pathogenic autoreactivity and autoimmune disease: leaky central negative selection allowing the escape of higher numbers of autoreactive precursors; impaired peripheral tolerance due to abnormalities involving receptors or ligands that mediated down-regulation of lymphocyte activity; a bias to generate Th1 pro-inflammatory responses as opposed to more balanced Th1/Th2 responses; high frequency and abnormal activity of professional APCs. Local inflammation and direct destruction of host cells trigger antigen release, uptake by professional APCs and presentation to specific T cells, thus perpetuating a positive feed-back that exacerbates the autoimmunity. Simultaneously, normally cryptic, organ-associated antigens may become exposed in the context of activation of professional antigen presenting cells and antigen release, resulting in activation of T cells specific for these other self antigens. Particularly in conditions favoring overall Th1/Th2 imbalance, the employment of additional specificities may accelerate the disease. One example of an autoimmune disease is type I diabetes.

In one debilitating autoimmune disease, insulin-dependent diabetes mellitus (IDDM, type I diabetes or juvenile diabetes), the immune system attacks the insulin-producing beta cells in the pancreas and destroys them. A person with IDDM produces little or no natural insulin and requires daily injections of the hormone to stay alive. Each year, from 11,000 to 12,000 children are diagnosed with IDDM and, among the more than 7 million people in the United States who are being treated for diabetes, about 5 to 10 percent have IDDM. In young people, acute complications due to inadequately controlled glucose fluctuations pose the greatest threat to survival for people with IDDM. As people grow older, long-term complications resulting from damage to organs due to blood vessel deterioration become more important, resulting in, for example, peripheral neuropathy, nephropathy, and retinal degeneration.

In addition to protecting offspring by programming their immune defenses in utero, the disclosure also provide methods and compositions to prevent metabolic diseases and disorders in an immunized and vaccinated subject. Such methods and compositions utilize similar or identical antigens.

Insulin resistance, for example, is a condition in which cells, in particular adipocytes (fat cells) and muscle cells, exhibit decreased sensitivity to insulin. Insulin resistance is a defining characteristic of the metabolic syndrome that is often associated with obesity, and is involved in the onset of hypertension and the progression of arteriosclerosis. As stated above, type II diabetes is a metabolic disorder that is characterized by insulin resistance and impaired glucose-stimulated insulin secretion in pancreatic beta cells. The current theory of the pathogenesis of Type II diabetes is often referred to as the "insulin resistance/islet cell exhaustion" theory. According to this theory, a condition causing insulin resistance compels the pancreatic islet cells to hypersecrete insulin in order to maintain glucose homeostasis (resulting in hyperinsulinemia). After many years of hypersecretion, the islet cells eventually fail and the symptoms of clinical diabetes become manifest. It is important to note that it is not possible to determine the origin of insulin resistance once it is established since the onset of peripheral hyperinsulinemia leads to a condition of global insulin resistance.

Multiple environmental and genetic factors are involved in the development of insulin resistance, hyperinsulinemia and type II diabetes. An important risk factor for the development of insulin resistance, hyperinsulinemia and type II diabetes is obesity, particularly visceral obesity and phospholipid metabolism.

The isolation of potentially immunogenic peptides from MHC molecules is known in the art (See, Falk, et al., 1990, Nature 348:248-251; Rotzsche, et al., 1990, Nature 348:252-254; Elliott, et al., 1990, Nature 348:191-197; Falk, et al., 1991, Nature 351:290-296; Demotz, et al., 1989, Nature 343: 682-684; Rotzsche, et al., 1990, Science 249:283-287; the disclosures of which are incorporated herein by reference). Briefly, MHC-peptide complexes may be isolated by a conventional immunoaffinity procedure. The peptides then may be eluted from the MHC-peptide complex by incubating the complexes in the presence of about 0.1% TFA in acetonitrile. The eluted peptides may be fractionated and purified by reverse phase HPLC. The amino acid sequences of the eluted peptides may be determined either by manual or automated amino acid sequencing techniques known in the art. Once the amino acid sequence of a potentially protective peptide has been determined, the peptide may be synthesized in any desired amount using conventional peptide synthesis or other protocols known in the art.

Peptides having the same amino acid sequence as isolated peptides may be synthesized by solid-phase peptide synthesis using procedures similar to those described by Merrifield, 1963, J. Am. Chem. Soc., 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an α-carboxy group of an N-α-protected amino acid that has been activated by reacting it with a reagent such as dicyclohexyl-carbodiimide. The attachment of a free amino group to the activated carboxyl leads to peptide bond formation. The most commonly used N-α-protecting groups include Boc which is acid labile and Fmoc which is base labile.

Antigens or antigenic portions thereof can be selected for use as antigenic molecules to generate an immune response (immunogenicity). To determine the ability of a molecule to induce an immune reaction and/or to generate/react with antibodies, various techniques are known in the art. To determine immunogenicity or antigenicity by detecting binding to an antibody, various immunoassays known in the art can be used including, but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in vivo immunoassays (using colloidal gold, enzyme or radioisotope labels, for example), western blots, immunoprecipitation reactions, agglutination assays (e.g., gel agglutination assays, hemagglutination assays), complement fixation assays, immunofluorescence assays, protein A assays, and immunoelectrophoresis assays, and the like. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Methods known in the art for detecting binding in an immunoassay and are envisioned for use. In one embodiment for detecting immunogenicity, T cell-mediated responses can be assayed by standard methods, e.g., in vitro cytoxicity assays or in vivo delayed-type hypersensitivity assays.

Potentially useful antigens or derivatives thereof for use as antigenic molecules can also be identified by various criteria, such as the antigen's involvement in neutralization of a pathogen's infectivity or reduction in disease progression or spread (wherein it is desired to treat or prevent infection by such a pathogen) (Norrby, 1985, Summary, in Vaccines B S, Lerner, et al. (eds.), Cold Spring Harbor Laboratory, Cold Spring Harbor, N.Y., pp. 388-389), type or group specificity, recognition by patients' antisera or immune cells, and/or the demonstration of protective effects of antisera or immune cells specific for the antigen. In addition, where it is desired to treat or prevent a disease caused by pathogen, the antigen's encoded epitope typically displays a small or no degree of antigenic variation in time or amongst different isolates of the same pathogen.

Where it is desired to prevent a cell proliferative disorder such as cancer, known tumor-specific antigens or fragments or derivatives thereof are used to produce a protective immunity in offspring by immunizing the mother. For example, such tumor specific or tumor-associated antigens include, but are not limited to, KS ¼ pan-carcinoma antigen (Perez and Walker, 1990, J. Immunol. 142:3662-3667; Bumal, 1988, Hybridoma 7(4):407-415); ovarian carcinoma antigen (CA125) (Yu, et al., 1991, Cancer Res. 51(2):468-475); prostatic acid phosphate (Tailer, et al., 1990, Nucl. Acids Res. 18(16):4928); prostate specific antigen (Henttu and Vihko, 1989, Biochem. Biophys. Res. Comm. 160(2):903-910; Israeli, et al., 1993, Cancer Res. 53:227-230); melanoma-associated antigen p97 (Estin, et al., 1989, J. Natl. Cancer Inst. 81(6):445-446); melanoma antigen gp75 (Vijayasardahl, et al., 1990, J. Exp. Med. 171(4):1375-1380); high molecular weight melanoma antigen (Natali, et al., 1987, Cancer 59:55-63) and prostate specific membrane antigen.

Where it is desired to prevent viral diseases, molecules comprising epitopes of known viruses are used. For example, such antigenic epitopes may be prepared from viruses including, but not limited to, hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II).

Where it is desired to prevent bacterial infections, molecules comprising epitopes of known bacteria are used. For example, such antigenic epitopes may be prepared from bacteria including, but not limited to, *mycobacteria, rickettsia, mycoplasma, neisseria* and *legionella*.

Where it is desired to prevent protozoal infections, molecules comprising epitopes of known protozoa are used. For example, such antigenic epitopes may be prepared from protozoa including, but not limited to, *leishmania, kokzidioa*, and *trypanosoma*.

Where it is desired to prevent parasitic infections, molecules comprising epitopes of known parasites are used. For example, such antigenic epitopes may be from parasites including, but not limited to, *chlamydia* and *rickettsia*.

The methods and compositions of the disclosure can also be used to treat inflammatory reactions including those associated with vascular disease and autoimmune diseases (e.g., diabetes). For example, atherosclerosis is a chronic inflammatory process of the arterial wall and the underlying cause of most myocardial infarctions and ischemic strokes. The prevalence in atherosclerotic lesions of immune cells, in particular monocyte/macrophages and T cells, and their secretory products (e.g. interleukins, chemokines, growth factors, metalloproteinases), as well as evidence obtained in gene-targeted experimental models suggest that proinflammatory immune mechanisms promote atherosclerosis. Antigens present in atherosclerotic lesions, such as oxidized low-density lipoprotein (OxLDL), heat shock proteins, and others also trigger humoral immune responses capable of influencing disease progression, albeit in opposite directions. LDL, the main source of arterial cholesterol, undergoes significant oxidation in vivo and is then recognized and rapidly taken up by scavenger receptors of macrophages, resulting in foam cell formation, a hallmark of the disease. OxLDL is highly immunogenic. Circulating antibodies to various "oxidation-specific" epitopes are present in humans and animals models and may serve as indicators or predictors of the disease. Diabetes is accompanied by increased nonenzymatic glycation, i.e. a modification of proteins by elevated concentrations of reactive sugars. Nonenzymatic glycation and lipid peroxidation are mutually reinforcing. Consequently, oxidative stress and inflammation are substantially increased in diabetes and in turn, increased oxidative stress may promote type 2 diabetes. The disclosure demonstrates that increased lipid peroxidation and oxidative stress are not only associated with increased atherosclerosis, but also with the onset of insulin resistance.

Immunization of rabbits and mice with various models of OxLDL consistently reduced the progression of atherosclerosis and diabetes. Both humoral and cellular mechanisms have been proposed. For example, immunizations with homologous MDA-LDL (i.e. LDL conjugated in vitro with malondialdehyde, one of the many reactive aldehydes generated during lipid peroxidation), or CuOx-LDL (i.e. LDL oxidized by incubation with copper ions), induced high titers of antibodies. Such antibodies may form immune complexes with circulating LDL bearing some oxidation-specific epitopes, and thus remove them from the circulation. In addition, cellular mechanisms have been postulated, including a switch from Th1 cells (secreting proatherogenic interferon γ) to Th2 cells (secreting anti-atherogenic interleukins, such as IL-10 and IL-13). The role of antibodies to oxidation-specific epitopes in atherosclerosis was further elucidated when it was discovered that a number of monoclonal IgM antibodies cloned from non-immunized atherosclerotic apoE mice (e.g., EO6) were identical to the classical T15-idiotype anti-phosphorylcholine antibodies that convey protection against pneumococcal infections. Natural T cell independent antibodies of the T15 idiotype are generated by B-1 lymphocytes, and are part of the innate immune response that was believed not to vary in response to antigen contact. As predicted by the immunological cross-reactivity between Cu-LDL, oxidized phospholipids, and membrane antigens of *S. pneumoniae*, immunization with the latter also reduced atherogenesis, raising the possibility of immunological interactions between atherosclerosis and bacterial infections and between innate and cognate immune mechanisms to oxidative neoepitopes.

Hypercholesterolemia and oxidative stress also play an important pathogenetic role in the fetal programming of atherosclerosis and diabetes. In humans, maternal hypercholesterolemia is associated with increased fatty streak formation in fetal arteries and accelerated progression of atherosclerosis during normocholesterolemic childhood. The maternal subject is also at risk of adult onset diabetes during pregnancy due to changes in metabolism and weight gain in the subject.

Increased atherosclerosis in offspring of hypercholesterolemic mothers could not be explained by conventional risk factors and suggested a pathogenic role of in utero conditions. Experiments in genetically more homogeneous models have since established that temporary, diet-induced hypercholesterolemia of mothers during pregnancy is indeed sufficient to enhance fetal lesion formation, to increase the postnatal susceptibility to conventional risk factors, and to cause persistent changes in arterial gene expression. Maternal treatment with cholesterol-lowering agents or antioxidants greatly reduced both fetal and postnatal atherogenesis, indicating a pathogenic role of lipid peroxidation and a potential involvement of oxidation-sensitive signaling pathways. Thus, fetal programming events induced by maternal hypercholesterolemia and increased oxidative stress determines adult atherogenesis, and these pathogenic events are amenable to therapeutic interventions during pregnancy.

Classical T cell mediated autoimmune diseases include rheumatoid arthritis (RA), multiple sclerosis (MS), Sjogrens, sarcoidosis, insulin dependent diabetes mellitus (IDDM), autoimmune thyroiditis, reactive arthritis, ankylosing spondylitis, scleroderma, panmyositis, dermatomyositis, psoriasis, vasculitis, Wegner's granulomatosis, Crohn's disease and colitis. Each of these diseases is typically characterized by high affinity T cell receptors that bind to endogenous antigens and initiate the inflammatory cascade associated with autoimmune diseases. Vaccination against the variable region of the high affinity T cells would elicit an immune response including CTLs to eliminate those T cells. The methods and compositions of the disclosure can be useful for treating any of these or other autoimmune diseases. At present, immunizations are administered only after the onset of clinical manifestations of autoimmune disease, i.e. when irreversible damage (e.g., to the pancreatic beta cells) has already occurred. In contrast, protection achieved through maternal immunization or immune stimulation should already be effective at the time that co-factors trigger an autoimmune attack.

In rheumatoid arthritis, several specific variable regions of T cell receptors (TCRs) which are involved in the disease have been characterized. These TCRs include Vbeta-3,beta-14, Vbeta-17 and Valpha-28. Thus, vaccination of a maternal subject with a construct that encodes or a composition that comprises at least one of these polypeptides will elicit an immune response that can target T cells involved in RA (See, e.g., Howell, M. D., et al., 1991 Proc. Natl. Acad. Sci. USA 88:10921-10925; Paliard, X., et al., 1991 Science 253:325-329; Williams, W. V., et al., 1992 J. Clin. Invest. 90:326-333; each of which is incorporated herein by reference).

In multiple sclerosis, several specific variable regions of TCRs which are involved in the disease have been characterized. These TCRs include Vbeta-7 and Valpha-10. Thus, vaccination of a maternal subject with a construct that encodes or a composition which comprises at least one of these proteins will elicit an immune response that can target T cells involved in MS in the offspring of the subject (See, e.g., Wucherpfennig, et al., 1990 Science 248:1016-1019; Oksenberg, et al., 1990 Nature 345:344-346; each of which is incorporated herein by reference). Candidate antigens for the methods of the disclosure also include myelin basic protein, lipoproteins, transaldolase, 2'3' cyclic nucleotide 3' phosphodiesterase, myelin oliodendroglial glycoprotein and myelin-associated glycoprotein.

In scleroderma, several specific variable regions of TCRs which are involved in the disease have been characterized. These TCRs include Vbeta-6, Vbeta-8, Vbeta-17 and Valpha-16. Thus, vaccination of a maternal subject with a construct that encodes or a composition that comprises at least one of these polypeptides will elicit an immune response that can target T cells involved in scleroderma in offspring of the subject.

B cell mediated autoimmune diseases include Lupus (SLE), Grave's disease, myasthenia gravis, autoimmune hemolytic anemia, autoimmune thrombocytopenia, asthma, cryobulinemia, primary biliary sclerosis and pernicious anemia. Each of these diseases is characterized by antibodies which bind to endogenous antigens and initiate the inflammatory cascade associated with autoimmune diseases.

In the case of IDDM, antigens include the insulin B chain or partial or whole insulin, glutamic acid decarboxylase (GAD65/67), islet cell antigens (IAs)—and heat shock protein (HSP60). In one embodiment, an insulin B chain is utilized for vaccination purposes. At any given level of plasma cholesterol, the risk for atherosclerosis is increased several-fold by diabetes. Furthermore, chronically elevated glucose levels also lead to modification of lysine residues of proteins and LDL, similar to that caused by reactive aldehydes generated by lipid peroxidation, and give rise to "advanced glycation endproducts" (AGE). Glycated proteins trigger autoimmune responses, in analogy to OxLDL, and macrophages have receptors for AGE. Glycation and oxidation enhance each other (and are therefore referred to as "glycoxydation"), and oxidative stress is therefore particularly great in diabetic subjects. Data provided demonstrate that the anti-atherogenic effect of maternal intervention was greatest in animal mothers that had the highest cholesterol levels and greatest oxidative stress. Maternal immunization can therefore be particularly beneficial in diabetes. Accordingly, immunization with oxidative neoepitopes of a lipoprotein (i.e., adducts between lysine or histidine residues and lipid peroxidation products or reactive sugars) are useful in the methods of the disclosure. Antigens therefore include circulating "native" LDL and all forms of "minimally modified LDL". Antigens also contain oxidized phospholipids and phospholipid-phospholipid adducts. Finally, antigens contain any chemical structure that comprises any of the above.

Another condition where similar events occur is pre-eclampsia, a pregnancy condition characterized by inflammation and atherosclerosis-like lesions rich in OxLDL in placental arteries. Accordingly, the methods of the disclosure utilizing OxLDL vaccines in maternal subjects can provide benefits.

Maternal immunization should also benefit postnatal conditions wherein high cholesterol levels are associated with an inflammatory condition, such as aortic aneurysm formation (Palinski W., Nat. Med. 2004; 10:896-8), and graft disease (transplant atherosclerosis).

As identified herein, the methods and compositions of the disclosure for fetal immune programming can include the induction of protective immunity to various pathogenic organisms, as well as preventing or attenuating other adult diseases modulated by the immune system. For example, it is possible to use maternal immunization to reduce atherosclerosis in the offspring of the maternal subject through the process of fetal immune programming.

In addition, the disclosure further demonstrates that the immunization of subject with oxidized lipoprotein antigenic agents can be used to reduce the risk or treat insulin resistance and associated diabetic conditions.

As described more fully below, in an exemplary process, reduction of atherosclerosis and insulin resistance was achieved through the process of immune modulation (adult and fetal). The effect of maternal immunization on humoral immune responses in offspring (e.g., the reduction of atherosclerosis or diabetes) has been demonstrated. The disclosure also demonstrates the effect of maternal interventions on various antibody populations, immune complexes, and selected T cell cytokines, and provides evidence for functional differences in immune responses between offspring of immunized and control mothers. Furthermore the disclosure demonstrates that fetal immune programming is independent of the maternal/fetal cholesterol levels during pregnancy.

In one aspect of the disclosure, in utero-programmed protective immunity is provided. Such a method comprises administering to a pregnant or soon to be pregnant female a composition comprising an antigen that induces protective immunity in the female subject. The composition comprising the antigen may include adjuvants and the like to assist in eliciting and immune response. In one aspect of the disclosure, the fetal programmed immunity provides protective immunity to the fetus following birth until adulthood, or throughout the lifespan of the programmed subject.

In some aspect, it is contemplated that although the maternal subject is immunized to induce fetal programming a "boost" vaccination or immunization can be performed in the offspring. The boosting vaccine is administered in an amount effective for "boosting" a primed immune response to an antigen. As used herein, "boosting" an immune response means to induce a secondary immune response in a subject that has been primed by an initial exposure to an antigen or programmed in utero by maternal adaptive immunity. A secondary immune response is characterized by the activation and expansion of specific memory T cells and B cells. Thus, boosting a specific immune response augments the primed immune response by inducing immune cells to proliferate and differentiate upon subsequent exposure to that antigen.

Fetal immune programming can be obtained using any number of antigens described herein. For example, administration of an antigen, either alone or in combination with an immune enhancing molecule or adjuvant, to a pregnant female or a female expecting or wanting to become pregnant can result in protective immunity to the offspring of the female. The antigen can be from any infectious microorganisms such as bacteria, fungi, yeast, *mycoplasma*, or viruses. Examples of appropriate microorganisms include, but are not limited to, *Salmonella enteriditis, Listeria monocytogenes, M. leprae, Staphylococcus aureus, Escherichia coli, Streptococcus pneumoniae, Borrelia burgdorferi, Actinobacillus pleuropneumoniae, Helicobacter pylori, Neisseria meningitidis, Yersinia enterocolitica, Bordetella pertussis, Porphyromonas gingivalis, mycoplasma, Histoplasma capsulatum, Cryptococcus neoformans, Chlamydia trachomatis, Candida albicans, Plasmodium falciparum, Entamoeba histolytica, Toxoplasma brucei, Toxoplasma gondii, Leishmania major*, human immunodeficiency virus 1 and 2, influenza virus, measles virus, rabies virus, hepatitis virus A, B, and C, rotaviruses, papilloma virus, respiratory syncytial virus, feline immunodeficiency virus, feline leukemia virus, and simian immunodeficiency virus. Mycoplasmal species include: *Mycoplasma hyopneumoniae* (swine); *M. hyorhinis* (swine); *M. hyosynoviae* (swine); *M. gallisepticum* (avian); *M. synoviae* (avian); *M. meleagridis* (avian); *M. gallinarum* (avian); *M. bovis* (bovine/caprine); *M. bovoculi* (bovine); *M. dispar* (bovine); *M. capricolumn* (caprine/bovine); *M. mycoides* subspecies *mycoides* (large colony (LC) and small colony (SC)) (ovine/caprine); *M. mycoides* subspecies *capri* (ovine/caprine); *M. agalactiae* (caprine/ovine); *M. pneumoniae* (human); *M. genitalium* (human); *M. penetrans* (human); *M. fermentans* (human); *M. hominis* (human); and all *Ureaplasma urealyticum* serotypes (human). Other relevant antigenic molecules include, without limitation, the B subunit of heat labile enterotoxin of *E. coli* (Konieczny et al. (2000) FEMS Immunol. Med. Microbiol. 27(4):321-332), heat-shock proteins, e.g., the *Y. enterocolitica* heat shock protein 60 (Mertz et al. (2000) J. Immunol. 164(3):1529-1537) and *M. tuberculosis* heat-shock proteins hsp60 and hsp70, the *Chlamydia trachomatis* outer membrane protein (Ortiz et al. (2000) Infect. Immun. 68(3):1719-1723), the *B. burgdorferi* outer surface protein (Chen et al. (1999) Arthritis Rheum. 42(9):1813-1823), the *L. major* GP63 (White et al. (1999) Vaccine 17(17):2150-2161), the *N. meningitidis* meningococcal serotype 15 PorB protein (Delvig et al. (1997) Clin. Immunol. Immunopathol. 85(2); 134-142), the *P. gigivalis* 381 fimbrial protein (Ogawa, (1994) J. Med. Microbiol. 41(5):349-358), and the *E. coli* outer membrane protein F (Williams et al. (2000) Infect. Immun. 68(5):2535-2545). Mycoplasmal immunogenic proteins include the P1 protein of *M. pneumoniae* and its homologs in *M. genitalium* and *M. gallisepticum*, the pMGA gene family in *M. gallisepticum*, surface lipoproteins that undergo antigenic variation such as the VSP proteins in *M. bovis*, the VLP proteins in *M. hyorhinis*, P78 in *M. fermentans*, and the VAA proteins in *M. hominis*. Furthermore, mycoplasmal glycolipids that play a role in pathogenesis can also be useful immunogenic molecules for the fusion agents of the disclosure.

Fetal immune programming can also be obtained using tumor antigens. As used herein, a "tumor antigen" is a molecule (e.g., a protein molecule) that is expressed by a tumor cell and either (a) differs qualitatively from its counterpart expressed in normal cells, or (b) is expressed at a higher level in tumor cells than in normal cells. Thus, a tumor antigen can differ (e.g., by one or more amino acid residues where the molecule is a protein) from, or it can be identical to, its counterpart expressed in normal cells. It is typically not expressed by normal cells. Alternatively, it is expressed at a level at least two-fold higher in a tumor cell than in the tumor cell's normal counterpart. Appropriate tumors include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such ovarian cancer, vaginal cancer, bladder cancer, testicular cancer, prostate cancer or penile cancer, bone tumors, and vascular tumors. Examples of tumor antigens include, but are not limited to, CEA, prostate specific antigen (PSA), MAGE (melanoma antigen) 1-4, 6 and 12, MUC (Mucin) (e.g., MUC-1, MUC-2, etc.), tyrosinase, MART (melanoma antigen), Pmel 17(gp100), GnT-V intron V sequence (N-acetylglucoaminyltransferase V intron V sequence), Prostate Ca psm, PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP) Bcl-2, and Ki-67.

Fetal immune programming can be obtained using any number of antigens described herein. For example, administration of an antigen, either alone or in combination with an immune enhancing molecule or adjuvant, to a pregnant female or a female expecting or wanting to become pregnant can result in protective immunity to the offspring of the female. In addition, the antigen can be an autoantigen involved in the initiation and/or propagation of an autoimmune disease, the pathology of which is largely due to the activity of antibodies specific for a molecule expressed by the relevant target organ, tissue, or cells, e.g., SLE or MG. In such diseases, it can be desirable to direct an ongoing antibody-mediated (i.e., a Th2-type) immune response to the relevant autoantigen towards a cellular (i.e., a Th1-type) immune response. Alternatively, it can be desirable to prevent onset of or decrease the level of a Th2 response to the autoantigen in a subject not having, but who is suspected of being susceptible to, the relevant autoimmune disease by prophylactically inducing a Th1 response to the appropriate autoantigen. Autoantigens of interest include, without limitation: (a) with respect to SLE, the Smith protein, RNP ribonucleoprotein, and the SS-A and SS-B proteins; and (b) with respect to MG, the acetylcholine receptor.

Also encompassed by the disclosure is the delivery of antigenic molecules to a female subject using gene therapy techniques. Such techniques include the delivery of recombinant DNA constructs encoding a polypeptide that induces an immune reaction. The DNA construct is delivered to the female subject wherein the DNA is expressed to produce the antigenic molecule. In certain aspects the DNA construct can comprise a fusion construct encoding a fusion protein comprising a first domain directed to an antigenic polypeptide and a second domain directed to an adjuvant/immune enhancing molecule, wherein the domains are operably linked.

Compositions comprising an antigen either alone or in combination with immune enhancing molecules/adjuvants and/or pharmaceutically acceptable carriers can be delivered to a female subject using any number of techniques known in the art to obtain an immune reaction and/or to immunize a subject. Furthermore, the fetal immune programming of an offspring from such a female can be assessed using common techniques in the art, including measuring antibodies directed to a particular antigen in the offspring's blood/serum.

Immune generating compositions for parenteral administration are contained in a "pharmaceutically acceptable carrier". Such carriers include sterile aqueous or non-aqueous solutions, suspensions and emulsions. Examples of non-aqueous solvents include propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, antioxidants, chelating agents, and inert gases and the like.

The term "pharmaceutically active substance" encompasses any substance that will produce a therapeutically beneficial pharmacological response when administered to a host, including both humans and animals. More than one pharmaceutically active substance may be included, if desired, in a pharmaceutical composition used in the method of the disclosure.

The pharmaceutically active substance can be employed in the disclosure in various forms, such as molecular complexes or pharmaceutically acceptable salts. Representative examples of such salts are succinate, hydrochloride, hydrobromide, sulfate, phosphate, nitrate, borate, acetate, maleate, tartrate, salicylate, metal salts (e.g., alkali or alkaline earth), ammonium or amine salts (e.g., quaternary ammonium) and the like. Furthermore, derivatives of the active substances such as esters, amides, and ethers, which have desirable retention and release characteristics but which are readily hydrolyzed in vivo by physiological pH or enzymes can also be employed.

As used herein, the term "therapeutically effective amount" or an "immunomodulatory effective amount" means that the amount of the pharmaceutically active substance is of sufficient quantity and activity to induce desired pharmacological effect which, in the this disclosure, is the immunopotentiation of an immune response to an epitope. The amount of substance can vary greatly according to the effectiveness of a particular active substance, the age, weight, and response of the individual host, as well as the nature and severity of the host's symptoms. Accordingly, there is no upper or lower critical limitation upon the amount of the active substance. The required quantity to be employed in the present invention can readily be determined by those skilled in the art.

By the term "regulating the immune response" or grammatical equivalents, herein is meant any alteration in any cell type involved in the immune response. The definition is meant to include an increase or decrease in the number of cells, an increase or decrease in the activity of the cells, or any other changes which can occur within the immune system. The cells may be, but are not limited to, T lymphocytes, B lymphocytes, natural killer (NK) cells, macrophages, eosinophils, mast cells, dendritic cells, or neutrophils. The definition encompasses both a stimulation or enhancement of the immune system to develop a sufficiently potent response to a deleterious target, as well as a suppression of the immune system to avoid a destructive response to a desirable target. In the case of stimulation of the immune system, the definition includes future protection against subsequent challenge (e.g., with a virus).

By the term "systemic immune response" or grammatical equivalents herein, is meant an immune response which is not localized, but affects the individual as a whole, thus allowing specific subsequent responses to the same stimulus.

By the term "co-administering" or grammatical equivalents herein, is meant a process whereby at least one self-antigen epitope and at least one cytokine or other biological response modifier are encountered by the individual's immune system at essentially the same time. The components need not be administered by means of the same vehicle. If they are administered in two separate vehicles, they must be administered sufficiently closely, both in time and by route of administration, that they are encountered essentially simultaneously by the individual's immune system to achieve the desired specificity. It should be understood that at least one epitope and at least one biological response modifier can be encoded on the same genetic construct or on more than one construct that is co-administered (e.g., same or different plasmids).

One of ordinary skill will appreciate that, from a medical practitioner's or patient's perspective, virtually any alleviation or prevention of an undesirable symptom (e.g., symptoms related to disease, sensitivity to environmental or factors, normal aging, and the like) would be desirable. Thus, "treatment", "therapeutic use", or "medicinal use" used herein refers to any and all uses of the claimed compositions which remedy a disease state or symptoms, or otherwise prevent, hinder, retard, or reverse the progression of disease or other undesirable symptoms in any way whatsoever.

An appropriate dosage of a vaccine or immunizing composition or genetic construct, may be determined by any of several well established methodologies. For instance, animal studies are commonly used to determine the maximal tolerable dose, or MTD, of bioactive agent per kilogram weight. In general, at least one of the animal species tested is mammalian. Those skilled in the art regularly extrapolate doses for efficacy and avoiding toxicity to other species, including human. Before human studies of efficacy are undertaken, Phase I clinical studies in normal subjects help establish safe doses. Alternatively, initial toxicity studies may involve individuals that are at the terminal stages of the disease progression.

These novel vaccine formulations can be administered in conventional solid or liquid pharmaceutical administration forms, e.g. uncoated or (film-) coated tablets, capsules, powders, granules, suppositories, or solutions. These are produced in a conventional manner. The active substances can for this purpose be processed with conventional pharmaceutical aids, such as tablet binders, fillers, preservatives, tablet disintegrants, flow regulators, plasticizers, wetting agents, dispersants, emulsifiers, solvents, sustained release compositions, antioxidants and/or propellant gases (cf. H. Sucker, et al. "Pharmazeutische Technologie". 1978. Thieme-Verlag, Stuttgart). The administration forms obtained in this way normally contain 1-90% by weight of the active substance.

Regardless of the epitope selected or the ultimate form in which it is delivered, (i.e. plasmids, viral vector, etc.), those skilled in the art will further appreciate that the effective treatment or induction of prophylaxis in a subject may include more than one inoculation.

It will be appreciated that the treatment or prevention of an autoimmune disorder does not require that the entire population of autoreactive cells be completely eliminated but rather that the population be reduced or an energized to the point of providing clinically beneficial effects. Besides a reduction in the severity of symptoms associated with a given autoimmune disorder, assays for quantitating autoreactive responses are well known and could easily be performed by those skilled in the art.

Similarly, the term "inoculating", as used herein, refers to administering or introducing a pharmaceutically acceptable composition incorporating an immunomodulating compound comprising at least one antigen or epitope. While an effective immune response may be induced with a single inoculation, the treatment of a subject may comprise multiple inoculations or a subsequent booster or boosters. As such, the methods of the present invention may comprise one, two, three, four or even five inoculations in order to achieve the desired immunoprophylactic effect.

Such antigens may be whole antigens, antigen fragments (obtained by molecular biology or biochemical techniques well known in the art) or peptides comprising single epitopes. The expressed epitopes may be associated with other natural products such as immunoglobulins or any natural or synthetic ligand for receptors on body cells. They may be administered as isolated, individual components or in mixtures. Examples for expressed epitopes that may be useful in the treatment of diabetes type I include, but are not limited to, such peptides and antigens as: GAD65 (glutamic acid decarboxylase 65-Baekkeskov et al., Nature 1990, 347:151), insulin (Palmer et al., Science 1983, 222:1337), ICA512/IA-2 (islet cell antigen 512; Rabin et al., J. Immunol. 1994, 152:3183). In the case of MS, such proteins and peptides are: MBP (myelin basic protein, Steinman et al., 1995, Mol. Med. Today, 1:79; Warren et al., 1995, Proc. Natl. Acad. Sci. USA, 92:11061).

PLP. transaldolase, 2',3' cyclic nucleotide 3' phosphodiesterases (CNP), MOG and MAG (Steinman L., 1995, Nature, 375:739). Besides autoimmune diseases, it will be appreciated that the compositions and methods of the present invention may also be used to down regulate immune responses provoked by allergens.

The working examples below are provided to illustrate, not limit, the disclosure. Various parameters of the scientific methods employed in these examples are described in detail below and provide guidance for practicing the disclosure in general.

EXAMPLES

An overview of the experiments is provided in Table 1.

TABLE 1

Overview of experimental design and groups

| Mothers Group | Immunization* | Diet Before and During Pregnancy[a] | Target Plasma Cholesterol (mg/dl) | Maternal Diet During Lactation | Offspring Experiments |
|---|---|---|---|---|---|
| NZW Rabbits | | | | | |
| Normocholesterolemic | None | Normal | 50 | 4% fat[d] | Atherosclerosis offspring of all groups fed hypercholesterolemic diet until age 6 months; target plasma cholesterol: 350 mg/dl |
| Hypercholesterolemic | None | Hypercholesterolemic | 350 | 4% fat[d] | antibody and immune complex determination at age 1, 3, 4, 5 and 6 months atherosclerosis measurement in the entire aorta at 6 months |
| Hypercholesterolemic + Vitamin E | None | Hypercholesterolemic | 350 | 4% fat[d] | splenocyte measurements at 6 months (ELISpot) |
| OXLDL-Immunized Hypercholesterolemic | OxLDL + FA | Hypercholesterolemic | 350 | 4% fat[d] | |
| OXLDL-Immunized Marginally Hypercholesterolemic | OxLDL + FA | Hypercholesterolemic | 350-not reached[b] | 4% fat[d] | Immune Challenge native offspring never exposed to hypercholesterolemia and other genesis, age 6 to 7 weeks or 6 months one-time s.c. injection of OxLDL and KLH |
| OXLDL-Immunized Normocholesterolemic | OxLDL + FA | Hypercholesterolemic | 50 | 4% fat[d] | determination of immune responses over 8 weeks |
| PBS + FA-Immunized Hypercholesterolemic | PBs + FA | Normal | 350 | 4% fat[d] | |
| LDLR Mice | | | | | |
| OxLDL-Immunized | OxLDL + FA | Normal | 250[c] | Normal | Atherosclerosis: Verification of antiatherogenic effect in both genders, various ages, and different sites: offspring of all groups fed hypercholesterolemic |
| PBS + FA-Immunized | PBS + FA | Normal | 250[c] | Normal | target plasma cholesterol 800 mg/dl female offspring: atherosclerosis measurement in cross-section of the aortic origin at age 20 weeks male offspring: measurement of atherosclerotic surface area in the entire aorta at age 34 weeks |
| Control | None | Normal | 250[c] | Normal | Immune Programming (in same animals) antibody and immune complex determinations at age 4, 12 and 20 weeks (females and males and 34 weeks (m) splenocyte measurements (ELISpot, FACS) peritoneal cell measurements (FACS) |
| KLH-immunized | KLH | Normal | 250[c] | Normal | Immune Programming: native, chow-fed offspring,, age 6 weeks |

TABLE 1-continued

Overview of experimental design and groups

| Mothers Group | Immunization* | Diet Before and During Pregnancy[a] | Target Plasma Cholesterol (mg/dl) | Maternal Diet During Lactation | Offspring Experiments |
|---|---|---|---|---|---|
| Control | None | Normal | 250[c] | Normal | single s.c. injection of KLH determination of immune responses over 6 weeks |

*Primary immunization at age 6 weeks. Two boosters at age 8 and 10 weeks. Determination of antibody titers at 12 weeks. All rabbit mother were regular diet during immunization;
[a]Cholesterol content of hypercholesterolemic diet was individually adjusted to keep plasma cholesterol within target range: TC determination at 3 weeks intervals;
[b]Actual level reached: 109 mg/dl;
[c]Spontaneous level of chow-fed LDLR--mice;
[d]Basic diet (4%, 17% protein, 57% carbohydrate, 17% fibers) later supplemented with cholesterol and administered to offspring of the atherosclerosis experiment.

Experimental Design—Rabbits. To investigate whether prior immunization with OxLDL reduces the atherogenic effect of maternal hypercholesterolemia during pregnancy, 7 groups of female NZW rabbits (Charles River) were used ("mothers")(n=42, total). Three of these served as non-immunized controls: 1) Mothers fed regular rabbit chow before, during, and after pregnancy ("Normocholesterolemic"); 2) mothers fed an atherogenic diet supplemented with individually adjusted cholesterol, in order to achieve plasma cholesterol levels at approximately 350 mg/dl before and during pregnancy ("Hypercholesterolemic"); and 3) mothers fed the same individually adjusted cholesterol-enriched diet together with a high dose of vitamin E (10 g α-tocopherol/kg diet, equivalent to approximately 400 IU/kg BW/day (1 g=1360 IU), Sigma) ("Hypercholesterolemic+Vitamin E"). The remaining groups were immunized with OxLDL or PBS prior to inducing hypercholesterolemia and pregnancy (see below for details of immunogen and immunization procedure). Originally, only one OxLDL-immunized hypercholesterolemic group was planned. However, early on it became apparent that hypercholesterolemia within the target range could not be achieved in some of the OxLDL-immunized mothers, despite prolonged feeding of the diet supplemental with cholesterol (0.15%). Therefore, the protocol was expanded to include four immunized groups: 4) "OxLDL-immunized hypercholesterolemic" mothers; 5) Ox-LDL-immunized mothers that achieved only marginal hypercholesterolemia despite being fed hypercholesterolemic diet ("OxLDL-immunized Marginally Hypercholesterolemic"); 6) genuinely normocholesterolemic Ox-LDL-immunized mothers fed regular chow ("OxLDL-immunized Normocholesterolemic"); and 7) mothers immunized with PBS and Freund's adjuvant (FA), to control for the FA used for all OxLDL-immunizations ("PBS-immunized Hypercholesterolemic").

Blood samples for plasma lipid determinations offspring were obtained from an ear vein at approximate 4 week intervals, and samples for antibody and immune complex determinations at ages of 1, 3, 4.5, and 6 months. Experimental groups contained roughly equal numbers of males and females, and data for both sexes were analyzed together because previous studies had not indicated significant gender differences.

Maternal and offspring diets. Female NZW rabbits ("mothers"), approximate 6 weeks old, were fed a standard rabbit chow during the immunization procedure. Once a marked increase in antibody titer had been confirmed two weeks after the last boost, mothers in the hypercholesterolemic groups were fed an atherogenic diet containing approximately 9% fat, 17% protein, 57% carbohydrate, and 16% fibers (Harlan Teklad rabbit diet #7009 supplemented with 6.5% corn oil) with or without vitamin E. Initially, 0.15% cholesterol was added to the diet (dissolved in ether, sprayed onto food pellets, and thoroughly evaporated). Total plasma cholesterol (TC) was determined after two weeks and the cholesterol concentration added to the diet was individually adjusted (0.05-0.25%) until their TC was within the target range (300-400 mg/dl). Females were then mated, and TC during pregnancy was determined after 2.5 weeks. After delivery, all mothers were reverted to the diet later fed to offspring (Harlan Teklad Rabbit Diet #7009 supplemented with 1.5% corn oil) containing 4% total fat, 17% protein, 57% carbohydrate, and 16% fibers.

Offspring were weaned at 4 weeks and fed the above 4% fat diet, supplemented with individually adjusted cholesterol (range 0.05%-0.4%, with most animals receiving 0.15 or 0.20%), in order to achieve plasma cholesterol levels of approximate 350 mg/dl. This approach was to chosen to reduce the variability in cholesterol and atherosclerosis in the genetically non-homogeneous NZW model, and indeed yielded very similar time-averaged TC levels in all groups (FIG. 1B). Although the cholesterol amount administered to individual offspring varied, the cumulative dietary cholesterol exposure during the 5 months of dietary intervention was very similar in all groups (Normocholesterolemic, 0.175%; Hypercholesterolemic, 0.179%; OxLDL-immunized Hypercholesterolemic, 0.143%; Hypercholesterolemic+VitE, 0.158%; OxLDL-immunized Marginally Hypercholesterolemic, 0.197%, PBS-immunized Hypercholesterolemic 0.153%).

Experimental protocol—Mice. Three groups of female LDL receptor-deficient mice (established from Jackson Labs LDLR$^{-/-}$ mice bred-back into C57BL\6 for 10 generations), age 6-8 weeks, were immunized with homologous OxLDL (an analogous mixture of MDA- and CuOx-LDL as for rabbits), or PBS with Freund's adjuvant, and compared to non-immunized controls. After the primary immunization and 3 biweekly boosts, immune responses were ascertained by ELISA and mating occurred. All mothers were fed regular chow throughout immunization and pregnancy and had cholesterol levels of about 260 mg/dl prior to and 150 mg/dl during pregnancy. After weaning at age 4 weeks, offspring were fed a regular murine diet supplemented with 0.25% to 0.5% cholesterol for 16 weeks (females) or 30 weeks (males). Plasma cholesterol was measured at 4, 12, and 20 weeks in retro-orbital blood. In a separate study, two groups of mice were immunized with KLH or PBS without adjuvants. Naïve offspring of these mice were then subjected to a single immune challenge with KLH at age 6 weeks.

Immunization of mothers. To obtain a broad spectrum of oxidation specific epitopes, including both malondialdehyde (MDA)-lysine epitopes and oxidized phospholipid epitopes, an equal mixture of homologous MDA-modified LDL (MDA-LDL) and copper-oxidized LDL (CuOx-LDL) was used for immunization of rabbits and mice. LDL was isolated from spontaneously hypercholesterolemic WHHL rabbits or LDLR$^{-/-}$ mice fed a high-fat, high-cholesterol diet by sequential ultracentrifugation in the presence of antioxidants and antiproteolytic agents and extensively modified with MDA or copper-ions as previously described. LDL was tested for endotoxin levels by chromogenic *Limulus amoebocyte* assay (QCL-1000; BioWhittaker) and contained less than 2 ng lipopolysaccharides/mg protein. The primary immunization of rabbits consisted of inguinal subcutaneous injections of 200 μg OxLDL (protein) per kg body weight in phosphate-buffered saline (PBS), emulsified in an equal volume of complete Freund's adjuvant (CFA) (Sigma #F-5881). Three intramuscular booster immunizations with the same amount of antigen in incomplete Freund's adjuvant (IFA) (Sigma # F-5506) were carried out in biweekly intervals, and antibodies to MDA-LDL and CuOx-LDL were verified 1-2 weeks thereafter. Control groups were immunized with PBS and CFA/FA. Immunization protocols were analogous to those used in previous immunization studies of adult rabbits and mice.

Circulating antibodies to oxidation-specific epitopes, apo B-immune complexes, and total immunoglobulins. Offspring plasma aliquots were stored at −80° C., and circulating antibodies, immune complexes, and total immunoglobulin concentrations at all time points were determined at the end of the intervention period by chemiluminescence ELISA. Circulating IgG and IgM antibodies in rabbit plasma (1:250 dilution) binding to human MDA-LDL, Cu-LDL, and phosphorylcholine (PC) plated in 96-well microtiter plates (Thermo Labsystems) were detected using alkaline phosphatase (AP)-labeled goat anti-rabbit IgG (1:4000 dilution; Sigma #A3812) or goat anti-rabbit IgM (1:400 dilution; Southern Biotechnology Associates #4020-04), and LumiPhos 530. Circulating mouse antibodies binding to the same antigens were detected using AP-labeled goat anti-mouse IgG (γ-chain specific, Sigma #A-9688, dilution 1:36,000) or anti-mouse IgM (μ-chain specific, Sigma # A-3438, dilution 1:56,000). Chemiluminescence was determined in a MLX Microtiter Plate Luminometer (Dynex Technologies) and results reported as specific binding (e.g. binding to CuLDL divided by binding to native LDL). Circulating T15/EO6 antibodies in murine plasma (1:100 dilution) were determined by coating wells with 5 μg/ml of AB1-2 (an anti-T15 idiotype kindly provided by J. Kearney, University, University of Alabama) in TBS and detecting captured antibodies with biotinylated AB1-2 (1 μg/ml), followed by AP-labeled NeutroAvidin (Pierce Biotechnology) and Lumiphos. Purified E06 was used for constructing a standard curve, and results were reported as μg/ml plasma.

Total rabbit plasma IgM was determined with a rabbit IgM ELISA Kit (Bethyl Laboratories # E120-110) and a 1:5000 plasma dilution. Total rabbit IgG was determined by a competitive binding ELISA, using rabbit IgG as the plated antigen (5 μg/ml) and incubating each well with 25 μl of a 1:500 plasma dilution or various dilutions of a standard rabbit IgG (Bethyl # P120-201) together with 25 μl of AP-labeled goat anti-rabbit IgG. Total mouse plasma IgG and IgM was assessed using mouse Ig ELISA Kit (Bethyl Laboratories #E90-131 for IgG, 1:50,000 plasma dilution; #E90-101 for IgM, 1:500 plasma dilution). Total IgG and IgM were reported as mg/ml.

IgG and IgM immune complexes with LDL were measured by capturing rabbit apoB with monoclonal antibody MB47 or mouse apo B with monoclonal antibody LF5. Capturing antibodies were plated overnight at 5 μg/ml of MB47 and incubated for 1 hour with rabbit or mouse plasma (1:50 and 1:100 dilution in BSA-PBS, respectively). IgM and IgG bound were detected using AP-labeled anti-rabbit or anti-mouse mouse IgM or anti-IgG. Results were corrected for the amount of LDL captured from each plasma, determined in parallel wells, using a guinea-pig antiserum to rabbit apoB and AP-labeled anti-guinea pig IgG (Sigma, # A-5062) for rabbit plasma, and AP-labeled monoclonal antibody LF3 (that binds to a single epitope per apo B particle) for murine plasma. Antibodies LF3 and LF5 were generous gifts from Dr. S. G. Young, UCLA, Los Angeles.

Offspring immune challenge. Separate groups of offspring of OxLDL-immunized hypercholesterolemic and non-immunized normocholesterolemic NZW mothers, age 6-7 weeks, were fed the regular 4% fat diet not supplemented with cholesterol since weaning. These conditions were chosen to minimize confounding effects resulting from the persistence of maternal IgG (IgM does not cross the placenta), or from immune responses to postnatal hypercholesterolemia and atherogenesis. In a first experiment, offspring received a single subcutaneous injection of two antigens: 300 μg OxLDL in CFA and 100 μg keyhole limpet hemocyanin (KLH), a non-mammalian protein. Blood was drawn after 4 days and 1, 2, 4, 6, and 8 weeks. In later experiments, rabbits were challenged with the same amount of KLH, but 2 mg of OxLDL. Results with both doses of OxLDL were similar and were therefore pooled for statistical analysis.

Enzyme-linked immunospot (ELISpot) assay. 96-well MultiScreen-HA sterile nitrocellulose plates (Millipore) were coated overnight with/without antigen (rabbit or mouse OxLDL), or with capture antibodies for immunoglobulins, goat anti-rabbit IgM (Bethyl #A120-110A, 5 μg/ml in PBS, 50 μl/well), goat anti-rabbit IgG-Fc (Bethyl #A120-111A, 5 μg/ml). Rabbit and mouse splenocytes were isolated, and red blood cells lysed with ACK lysis buffer. Cells were then resuspended in RPMI medium supplemented with 10% FCS, HEPES, gentamicin, and beta-ME, and counted. Cells from individual rabbits and mice (or balanced pools from all mice in each group) were added at $1\times10^6$ cells/well and incubated for 22 hours at 37° C. under 5% $CO_2$. Cells were then washed off and OxLDL-specific or all IgM-secreting (i.e., spot-forming) cells were detected using biotinylated goat anti-rabbit IgM (Southern Biotech #4020-08, 2 μg/ml in 1% BSA-TBS), biotinylated goat anti-rabbit IgG(H+L)(Vector Labs #BA-1000, 2 μg/ml), or biotinylated rat anti-mouse IgM (BD Pharmingen #553406, 2 μg/ml in BSA-TBS), followed by HRP-Streptavidin (Zymed# 43-4323, 1:1000 dilution). Plates were developed for 15-20 min using the Tetramethylbenzidine (TMB) Membrane Peroxidase Substrate System (Kirkegaard & Perry Laboratories), and spots were quantified under a dissecting microscope or with an ImmunoSpot Image Analyzer (Cellular Technology). Results were calculated as IgM- or IgG-secreting cells (ISC) per $10^6$ cells or antigen-specific ISC as percent of all ISC.

T cell proliferation assay. A suspension containing $5\times10^6$ splenocytes/ml was prepared from rabbit or mouse spleens removed immediately after sacrifice. Triplicate 100 μl aliquots were then added to an equal volume of antigen (10 μg/ml native LDL, or 0.2, 1, 5, 10, or 25 μg/ml OxLDL in complete RPMI medium) or 50 ng/ml PMA plus 500 ng/ml ionomycin (to determine maximum stimulation) in sterile round-bottom 96 well tissue culture plates and incubated for 24 hours at 37° C. under 5% $CO_2$. After adding 10 μl $^3$H-thymidine (approximately 1 μCi/well), incubation was continued for 16 hours. Plates were then harvested with a Manual Harverster 96 (Tomtec, Hamden, Conn.) and counted in a 1205 Betaplate Liquid Scintillation Counter (Walac/Perkin Elmer).

Quantification of atherosclerosis. The extent of atherosclerosis in rabbits and mice was determined by computer-assisted morphometry. Rabbit aortas were perfusion-fixed in situ under physiologic pressure with formaldehyde-sucrose via a catheter inserted into the left ventricle, dissected, cleaned of adventitial tissue, Sudan IV stained, opened longitudinally, and pinned out flat on a black wax surface. Electronic images were captured with an 11 megapixel Nikon digital camera and the percentage of atherosclerosis determined by ImagePro 5.0 software. Murine atherosclerosis was determined in 11 equidistant cross-sections of the aortic origin stained by a modified Trichrome method, using a 11 megapixel Leitz DCX500 digital camera mounted on a Leitz DC5000 microscope to capture images. Results were expressed as the percentage of aortic surface covered by atherosclerotic lesions or mean cross-sectional lesion area.

The studies presented herein assessed whether active immunization of mothers would protect against fetal programming by maternal hypercholesterolemia, for example, by increased removal from the circulation of immune complexes with LDL containing oxidative neoepitopes, or by reducing the amount of antigen present during the critical period of maturation and differentiation of the neonatal immune system. As demonstrated herein, maternal immunization indeed conveyed marked antiatherogenic protection to offspring, but against expectation, the protective effect was not limited to offspring of hypercholesterolemic mothers; it was associated with persistent changes in specific postnatal immune responses to hypercholesterolemia or immune-challenge of naïve offspring, involving both IgM and IgG antibody populations and B and T cell responses. These results indicate that fetal programming influences adult adaptive or innate immune responses and that modulation of maternal adaptive immunity reduces atherogenesis.

The influence of maternal immune modulation on atherosclerosis in their offspring was first assessed in NZW rabbits. In this model, non-immunized and immunized mothers were exposed during pregnancy to normo- or hypercholesterolemic diets without or with antioxidants (FIG. 1A). Prospective hypercholesterolemic mothers were fed diets with individually adjusted cholesterol content (0.15-0.25%) until a target plasma cholesterol level of about 350 mg/dl was achieved, which was then maintained throughout mating and pregnancy. After birth, all mothers were switched to a regular 4% fat diet. After weaning, cholesterol levels in all offspring were maintained at about 350 mg/dl until age 6 months by fine-tuning the cholesterol supplementation of a low-fat diet (FIG. 1B). In offspring of non-immunized mothers, moderate maternal hypercholesterolemia of 339 mg/dl increased aortic atherosclerosis by 48%, compared to offspring of normocholesterolemic mothers (43.7±4.5% of the surface area, compared to 29.6±4.4%, P<0.05) (FIG. 1C). Supplementation of the hypercholesterolemic diet with vitamin E did not affect maternal cholesterol levels (FIG. 1B), but abolished the atherogenic consequences of maternal hypercholesterolemia (25.6±5.3% atherosclerosis; 41.5% less than in offspring of untreated hypercholesterolemic mothers; P<0.02).

To determine the effect of prior immunization on the atherogenicity of maternal hypercholesterolemia, groups of prospective mothers were immunized with OxLDL or PBS and a positive immune response (i.e. a marked increase in antibodies to oxidation-specific epitopes) was ascertained prior to administration of the hypercholesterolemic diets and pregnancy. The "OxLDL" immunogen consisted of a combination of homologous LDL modified in vitro with malondialdehyde, a major byproduct of lipid peroxidation, and LDL oxidized by copper-ions. The rationale for choosing such a broad antigen was to induce both MDA-lysine-specific antibodies and antibodies against oxidized phospholipids and phospholipid-protein adducts, including EO6/T15 idiotype IgM, and thus to avoid biasing the immune response towards specific epitopes or immunoglobulin classes that may exert distinct effects on atherogenesis. Surprisingly, even with maximum cholesterol supplementation (0.25%) of individual diets, some of the OxLDL-immunized mothers failed to reach the target plasma cholesterol level. As it was unknown whether this resulted from immune-complex-mediated elimination of some plasma LDL or merely reflected greater genetic resistance to hypercholesterolemia, these mothers and their offspring were treated as a separate group.

Compared to offspring of similarly hypercholesterolemic mothers, maternal immunization with OxLDL markedly reduced atherosclerosis in adult offspring by 52% (20.9±3.8% of the aortic surface vs. 43.7±4.5%; P<0.0001) (FIG. 1C). Lesions in this group also were 29% smaller than those of offspring of non-immunize normocholesterolemic mothers, although the difference failed to reach statistical significance (P=0.14). The antiatherogenic effect of OxLDL-immunization achieved in offspring of mothers that only reached marginal hypercholesterolemia (106 mg/dl) despite being fed the high-cholesterol diet, was almost identical (19.1±5.7%) e.g., 56% less than in offspring of hypercholesterolemic mothers (P<0.005) and 36% less than in offspring of normocholesterolemic mothers (P=0.14). Immunization of hypercholesterolemic mothers with PBS+FA was far less effective than immunization with OxLDL, but also reduced atherogenesis (to 30±3.2%, P<0.05), indicating that the protective effect was not specific for OxLDL.

Figure 5:
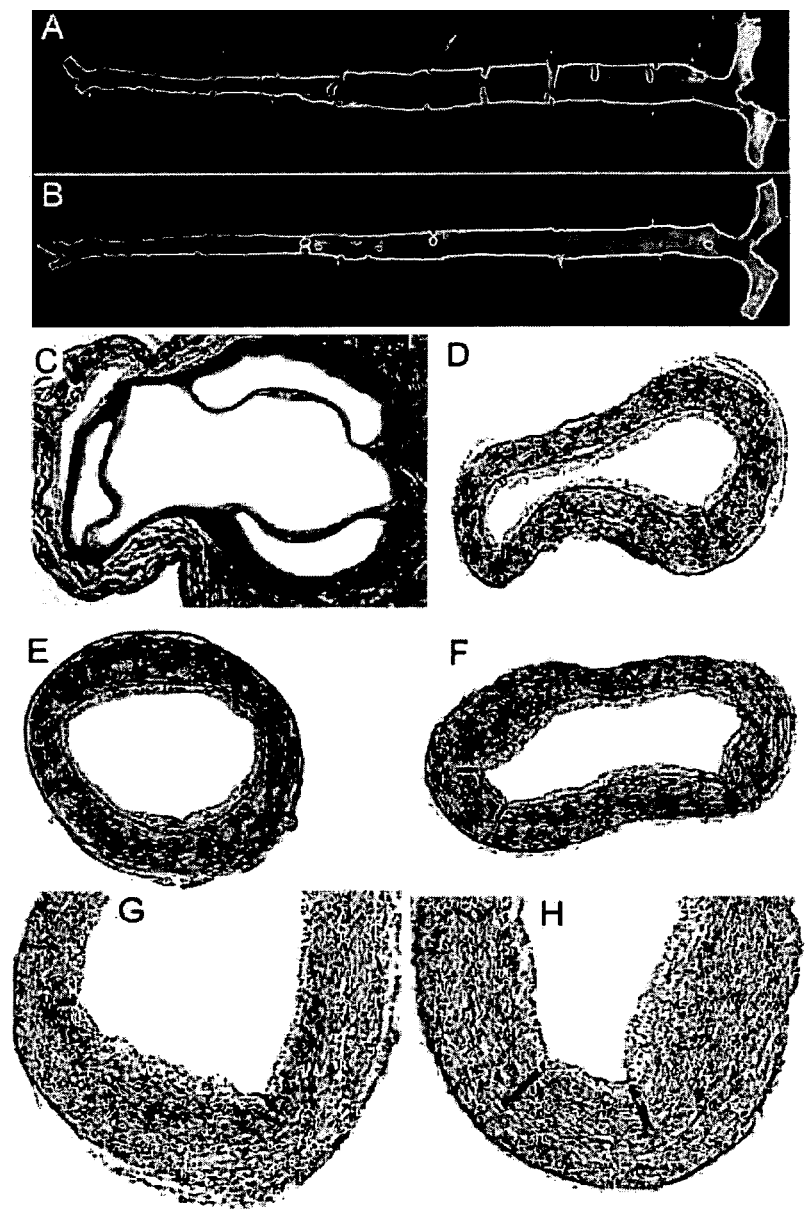
FIG. 5A-H are tissue sections that show maternal immunization with OxLDL does not appear to impact lesion formation during fetal development. In order to rule out that differences in postnatal atherogenesis stem from immune-modulation of cholesterol during pregnancy and its effects on fetal lesion formation, 15 offspring of hypercholesterolemic mothers were sacrificed within 3 days of birth and atherosclerosis was compared in cross-sections through the aortic origin and aortic arch and in Sudan stained en-face preparations of the entire aorta. At birth, all Sudan-stained aortas were free of macroscopic lesions, as shown for offspring of a PBS-immunized hypercholesterolemic (A) and an OxLDL-immunized hypercholesterolemic mother (B). No lesions were encountered in the aortic origin of either group (C). In contrast, microscopic lesions were prevalent in sections throughout the aortic arch of all newborn offspring of hypercholesterolemic mothers, but did not appear to be more extensive in the controls (D,G), and PBS group (E) than in the OxLDL-immunized group (F,H).

Given the marked atherogenic effect of maternal hypercholesterolemia previously established in this model and in humans, and confirmed here, the absence of differences in atherosclerosis between the OxLDL-immunized groups (FIG. 1C) was surprising, and indicated that the protective mechanism was not limited to the reduction of fetal exposure to hypercholesterolemia. Furthermore, it cannot be ascribed to the reduction of fetal lesions, because at birth no difference in microscopic aortic lesions was apparent between offspring of hypercholesterolemic mothers (FIG. 5).

Figure 2:
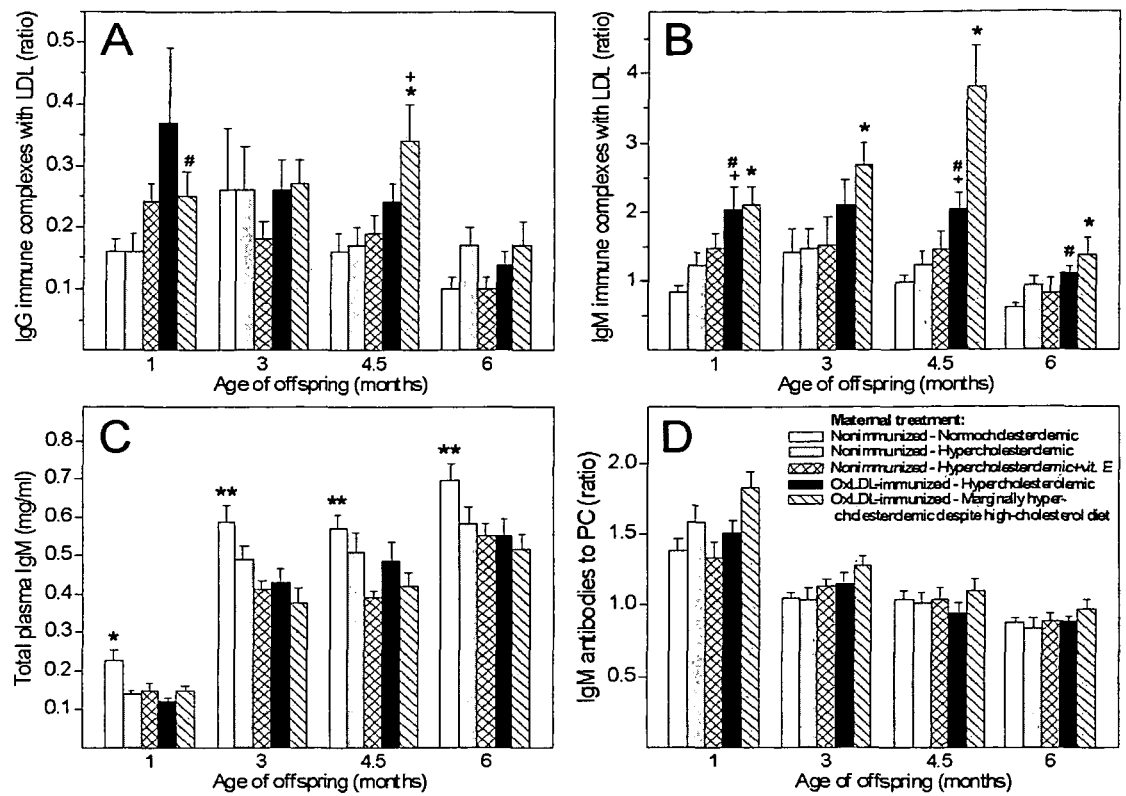
FIG. 2A-D shows maternal immunization of rabbits leads to persistent differences in circulating IgM-LDL immune complexes in offspring. (A) Circulating IgM-LDL immune complexes. LDL particles in a 1:50 dilution of plasma were captured in a sandwich chemiluminescence ELISA by an antibody to apoB (MB-47), and IgM bound to these particles was detected by a labeled anti-rabbit IgM antibody. Results are reported as LDL-IgM immune complexes corrected for the amount of LDL captured (i.e. divided by apoB bound to the plate). $*P<0.01$ and $^{\#}P<0.02$ vs. non-immunized normocholesterolemic $^{+}P<0.05$ vs. non-immunized hypercholesterolemic. (B) Total plasma IgM. Significances are only indicated between offspring of the non-immunized normocholesterolemic group and the marginally hypercholesterolemic group ($*P<0.05$; $**P<0.005$). Total IgM of the non-immunized normocholesterolemic group was also significantly greater than other groups at most time points. (C) Circulating IgM antibodies to MDA-LDL determined by chemiluminescence-ELISA. MDA-LDL was plated as antigen and incubated with a 1:250 dilution of plasma. Antibodies binding to the plated antigen were then detected by labeled anti-rabbit IgM. Results are reported as antibody binding to MDA-LDL divided by binding to native LDL. (D) Circulating IgM antibodies of the EO6/T15 idiotype (representing B1-cell derived innate immune responses), determined in analogy to panel C. Data in panels A-D represent triplicate determinations of all animals of the atherosclerosis study. See FIG. 1C for animal numbers in each group. Significances between time points (ANOVA) are not indicated.

To assess the effects of maternal hypercholesterolemia and/or immunization on postnatal immune responses to OxLDL, circulating antibodies and immune complexes in offspring were determined over time, in a single assay at the end of the study (FIG. 2). Plasma levels of circulating IgM immune complexes with LDL were consistently higher in offspring of OxLDL-immunized mothers than in controls, with the highest levels in offspring of mothers that developed only marginal hypercholesterolemia during pregnancy despite being fed a high-cholesterol diet (FIG. 2A). Compared to offspring of non-immunized normocholesterolemic mothers, the increase was highly significant at all but one time point in offspring of both extensively and marginally hypercholesterolemic OxLDL-immunized methods. (Immune complexes were not measured in OxLDL-immunized mothers, because this group followed the others in time.) These results were not affected by inter-individual differences in plasma LDL, because cholesterol levels were similar in all groups (FIG. 1B) and because immune-complex data were corrected for the binding of LDL to the ELISA plate. Results could also not be explained by differences in total IgM levels (FIG. 2B). Total IgM concentrations in all groups increased with age, but were lower in all offspring of hypercholesterolemic mothers, irrespective of immunization status. Total plasma IgG showed an analogous marked increase with increasing age, but did not indicate a consistent influence of maternal hypercholesterolemia.

None of the previously characterized populations of natural or induced oxidation-specific antibodies was consistently increased in offspring of immunized rabbits (FIGS. 2C, D). IgM antibodies to MDA-lysine epitopes showed differences between groups (FIG. 2C), suggesting that the increased formation (and removal from the circulation) of LDL-IgM immune complexes must either have compensated for any increase in IgM antibodies, or that it represents mainly IgM antibodies not binding to the antigens in the ELISAs. B-1 cell derived antibodies of the EO6/T15 idiotype showed a slight, statistically non-significant trend towards higher concentrations in offspring of OxLDL-immunized mothers (FIG. 2E). IgG antibodies to MDA-LDL and CuOx-LDL were also similar in all groups, and IgG-LDL immune complexes were not consistently changed over time. Together, these results suggest that the increase in circulating IgM-LDL immune complexes must largely be due to an as yet undefined population of IgM antibodies.

Figure 3:
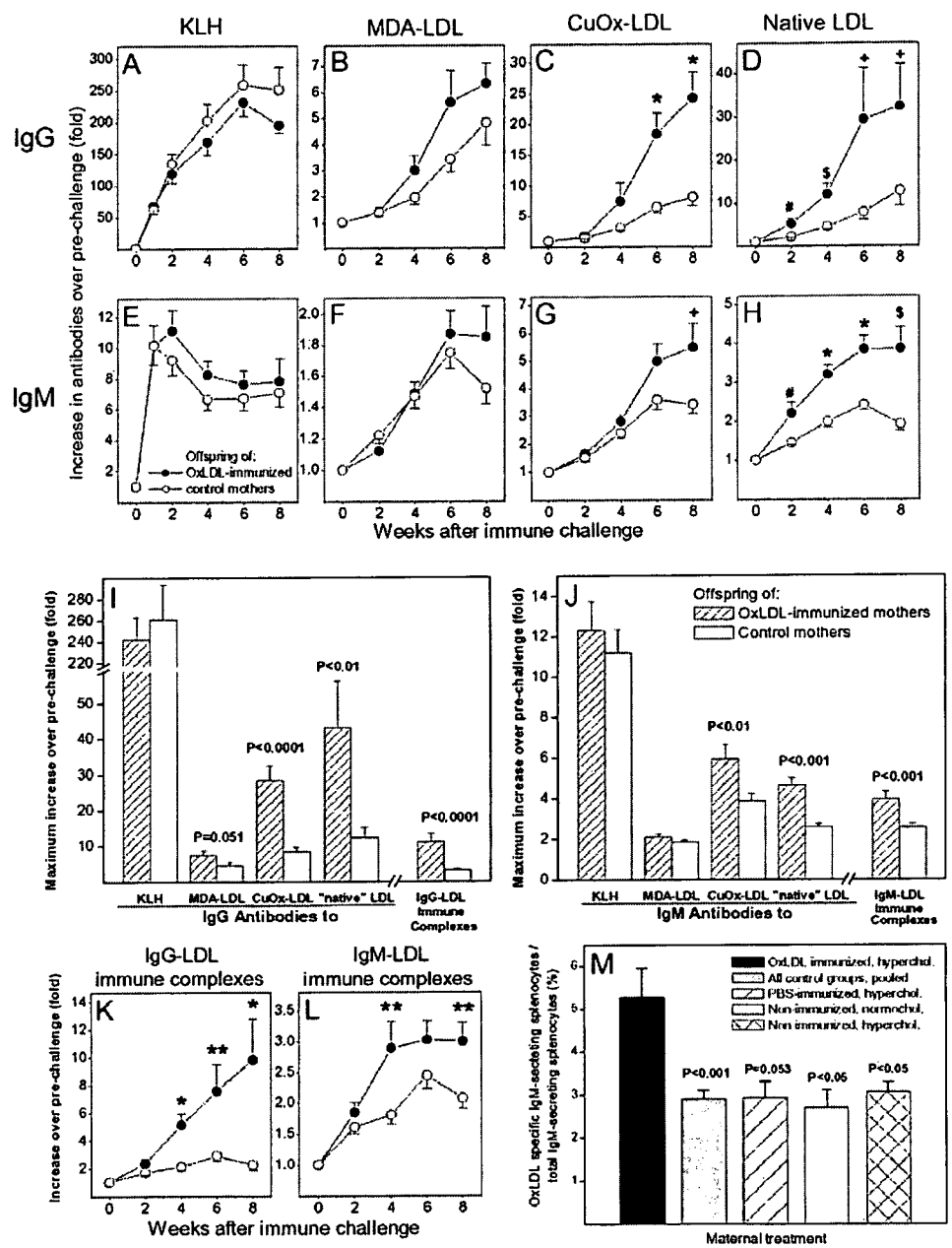
FIG. 3A-M shows maternal immunization influences IgG and IgM responses to an immune challenge with OxLDL in NZW offspring. Offspring of OxLDL-immunized hypercholesterolemic (n=15) and control mothers (non-immunized normocholesterolemic mothers and PBS-immunized hypercholesterolemic and normocholesterolemic mothers, n=22) were fed regular diet not supplemented with cholesterol since weaning, to avoid confounding effects of postnatal hypercholesterolemia and atherogenesis. At the age of about 6 weeks, rabbits received simultaneous subcutaneous injections of OxLDL and KLH into the left and right inguinal area. Circulating IgG (A-D) and IgM antibodies (E-H) to KLH, MDA-LDL, CuOx-LDL and "native" LDL were determined in triplicate by chemiluminescence ELISA (1:250 plasma dilution). Results are reported as relative increase over the pre-challenge antibody level. Because antibody levels peaked at different times, results are also shown as the maximum increase in each animal, irrespective of when it was reached (I,J). Immune complexes of IgG and IgM antibodies with LDL, determined by sandwich ELISA. LDL was captured from a 1:50 plasma dilution by a monoclonal antibody to rabbit apoB, and IgM bound to the captured LDL particles determined with an anti-rabbit IgM antibody. Results are reported as relative increases over pre-challenge levels (K,L). ELISpot analysis of splenic B cells secreting IgM in response to OxLDL stimulation, expressed as percentage of all IgM-secreting splenocytes.

Static measurements of antibody titers and immune complexes represent the balance of many factors, such as antibody formation, amount of antigen present, and removal of immune complexes. Evidence for an effect of maternal immunization on the immune system of offspring was therefore sought from a functional test, i.e. an immune challenge of offspring from OxLDL-immunized (hyper- and normocholesterolemic, n=17) and control mothers (PBS-immunized hypercholesterolemic and non-immunized hyper- and normocholesterolemic mothers n=22). All of these had been fed the regular 4% fat diet without added cholesterol since weaning, to avoid confounding effects of postnatal hypercholesterolemia and atherogenesis, and received simultaneous subcutaneous injections of OxLDL and keyhole limpet hemocyanin (KLH) at about 6 weeks of age. Results are reported as the relative increase of antibodies over their preimmune level (FIG. 3A-H). As expected, maternal immunization with OxLDL did not affect antibody responses to KLH. In both groups, IgG (FIG. 3A) and IgM antibodies (FIG. 3E) began to rise shortly after antigen injection and reached similar peaks after 2-3 weeks (IgM) or 6 weeks (IgG). IgG, and particularly IgM, responses to MDA-LDL, CuOx-LDL, and "native" LDL were slower and relatively weaker than those to KLH, but differences between groups began to emerge after 2 weeks. At 6-8 weeks, IgG and IgM responses to CuOx-LDL were markedly greater in offspring of OxLDL-immunized mothers than in controls (FIGS. 3C, G), indicating that the immune response to these epitopes was "primed" by maternal immunization with OxLDL. The differences started earlier and were even more significant for IgG and IgM antibodies to "native LDL (FIGS. 3D, H), whereas differences in antibodies to MDA-LDL did not reach significance (FIGS. 3B, F).

Similar results were obtained when data were compared on the basis of the maximum increase in antibody levels in each animal, irrespective of the time it was reached (FIGS. 3I, J). The fact that both IgM and IgG antibodies increased in parallel and to a much greater degree in offspring of OxLDL-immunized mothers than in controls is consistent with a secondary immune response. Together, these data suggest that the epitopes recognized by primed antibodies of primed offspring occur on LDL that is not extensively oxidized.

Circulating levels of IgG and IgM immune complexes with LDL (presumably oxidized to some extent) were also much greater in offspring of OxLDL-immunized mothers than those of control groups (FIGS. 3K, L). In analogy, differences in the maximum increase in immune complexes in each animal were highly significant (right-hand bars in FIGS. 3I, J). The difference in immune complexes was consistent with the increase in IgM immune complexes seen in the atherosclerosis experiment (FIG. 2A), and may again have attenuated the difference in circulating levels of oxidation-specific antibodies (FIGS. 3B-D and F-H), because the increases in free antibodies would be diminished by increased formation of immune complexes.

Figure 6:
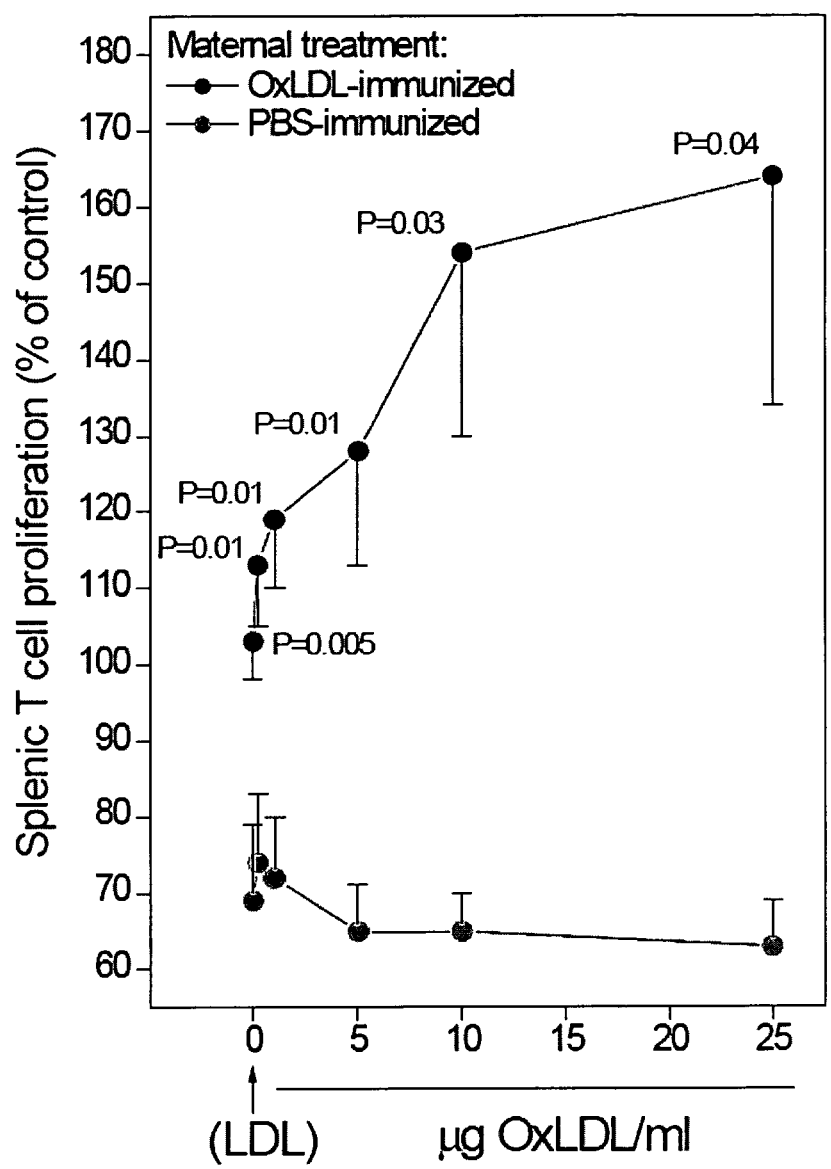
FIG. 6 demonstrates that maternal immunization with OxLDL leads to increased proliferation of splenic T-cells in response to OxLDL stimulation in offspring. Naïve NZW offspring never exposed to dietary hypercholesterolemia and atherogenesis were challenged by a simultaneous injection of KLH and OxLDL at age 6 weeks, and humoral immune responses were monitored for the following 8 weeks (see FIG. 3). Splenocyte preparations were then incubated with increasing concentrations of OxLDL as described below. A total of 28 rabbits from three groups were used in 4 time staggered-assays (offspring of OxLDL-immunized hypercholesterolemic mothers, n=11; PBS-immunized hypercholesterolemic mothers, n=5; and non-immunized normo- or hypercholesterolemic controls, n=12). To compensate for inter-assay variability, data of the OxLDL- and PBS groups were normalized by expressing them as percent of controls.

Splenic T-cell proliferation assays at the end of the immune challenge experiment (FIG. 6) indicated a significantly greater dose-dependent response to OxLDL in offspring of OxLDL-immunized mothers than offspring of PBS-immunized ones, consistent with the increased antibody production in the former.

As would be expected from the IgM antibody and immune complex data, ELISpot analysis of splenic lymphocytes isolated from 30 animals at the end of the immune-challenge experiment indicated a significantly greater percentage of splenocytes secreting OxLDL specific IgM in offspring of OxLDL-immunized mothers than in all controls (FIG. 3M). Maternal hypercholesterolemia or immunization with PBS and Freund's adjuvant did not affect the percentage of OxLDL-specific IgM-secreting B cells, compared to non-immunized normocholesterolemic controls.

Murine models are the obvious choice for further elucidation of fetal immune programming, given the far better genetic characterization of mice, the abundance of murine mRNA and cytokine arrays, and the availability of immune-deficient mice and crosses thereof with gene-targeted strains susceptible to atherosclerosis. To verify the effects of maternal adaptive immunity on offspring immune mechanisms and atherosclerosis, 35 offspring of female LDL receptor-deficient mice immunized with homologous OxLDL (an analogous mixture of MDA- and CuOx-LDL as used for rabbits), PBS with Freund's adjuvant, or non-immunized controls were compared. To avoid any confounding effects of maternal hypercholesterolemia, such as natural immune responses to increased LDL oxidation during pregnancy in non-immunized but hypercholesterolemic mothers, all murine mothers were fed regular chow throughout pregnancy. After weaning at age 4 weeks, offspring were fed a regular murine diet supplemented with 0.5% cholesterol for 4 months.

Figure 4:
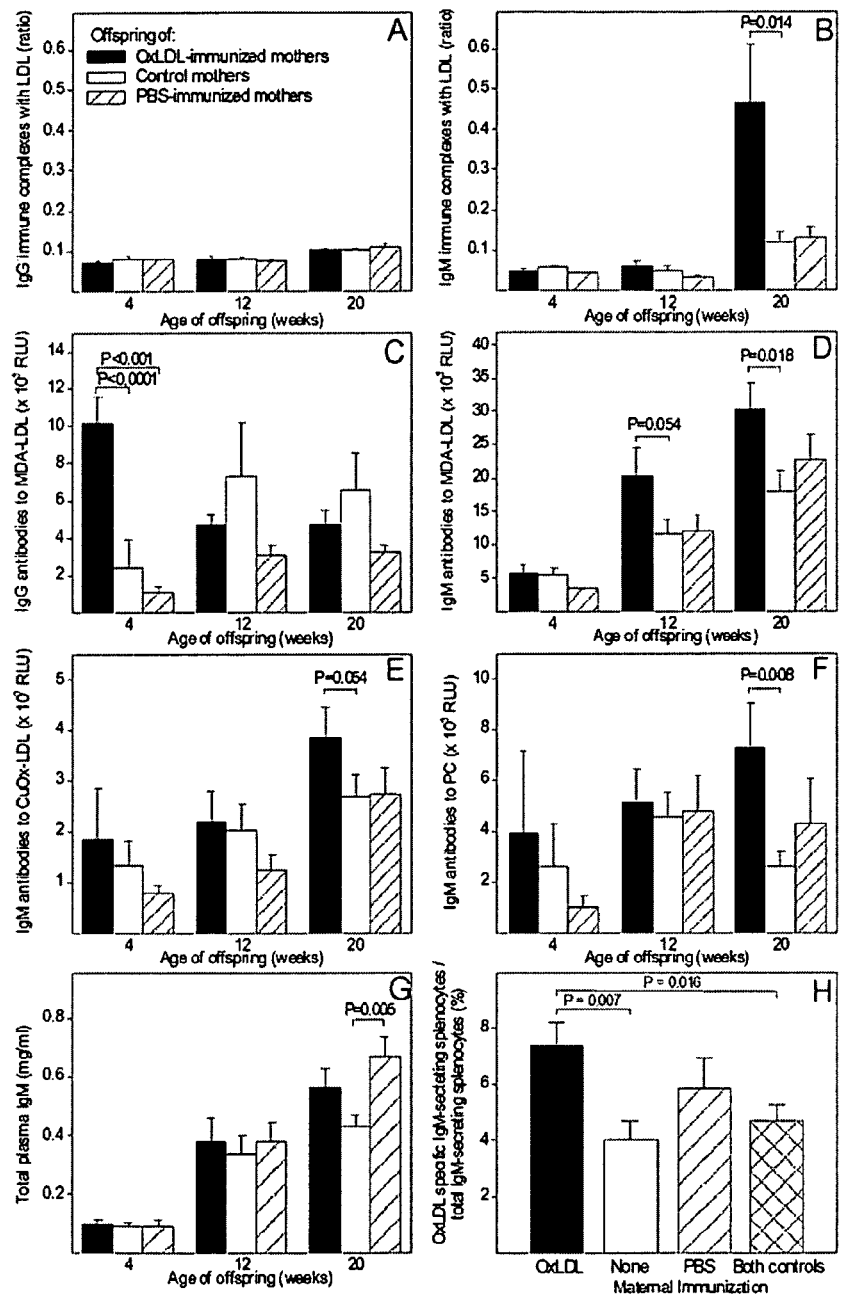
FIG. 4A-H shows maternal immunization influences spontaneous IgM antibody response, LDL immune complexes and IgM-secreting splenic B cells in LDLR$^{-/-}$ offspring. Female offspring of chow-fed mothers immunized with OxLDL (n=10), PBS+FA (n=5), or nonimmunized controls (n=13) were fed cholesterol-enriched regular chow from weaning. (A) Circulating IgG-LDL immune complexes and (B) IgM-LDL immune complexes. Results were corrected for the amount of apoB captured from each plasma. (C) IgG antibodies to MDA-LDL. Increased levels in offspring of OxLDL-immunized mothers at 4 weeks presumably reflect transplacental passage of high-titered maternal IgG. RLU, relative light units/100 ms. (D) IgM antibodies to MDA-LDL. (E) IgM antibodies to CuOx-LDL. (F) IgM antibodies to PC, an antigen recognized by innate EO6/T15 idiotype IgM antibodies. (G) Total plasma IgM. (H) ELISpot analysis of splenic B cells secreting anti-OxLDL IgM, expressed as percentage of all IgM secreting splenocytes.

Circulating antibody and immune complexes were determined at 4, 12, and 20 weeks and indicated marked differences between offspring of OxLDL-immunized and control mothers (FIG. 4). As expected, at the age of 4 weeks, IgG antibodies to MDA-LDL in offspring of OxLDL-immunized mothers greatly exceeded those in both controls, consistent with the active trans-placental transport of maternal IgG (FIG. 4A). In contrast, IgM antibodies to MDA-LDL were low and similar at birth, but began to differ at 12 weeks and were much greater in offspring of OxLDL-immunized than in non-immunized mothers at 20 weeks (FIG. 4B). Antibodies to PC (an antigen recognized by innate IgM antibodies of the EO6/T15 idiotype) showed analogous differences (FIG. 4C). However, direct measurements of circulating EO6/T15 antibodies revealed only a trend towards higher levels in offspring of OxLDL immunized mothers at 20 weeks. Consistent with the above increase in selected IgM antibody levels, circulating LDL-IgM immune complexes (FIG. 4D) were also markedly greater in offspring of OxLDL-immunized mothers at 20 weeks, whereas total IgM levels were not (FIG. 4F). ELISpot analysis also indicated a significantly greater percentage of Ox-LDL-specific IgM-secreting splenocytes in offspring of OxLDL-immunized mothers than in non-immunized controls, whereas offspring of PBS-immunized mothers displayed an intermediate level (FIG. 4F). Thus the effects of maternal OxLDL-immunization on spontaneous postnatal IgM immune responses in mice were more extensive than those in mildly hypercholesterolemic rabbit offspring and resembled those in normocholesterolemic rabbits following exogenous OxLDL immune challenge.

To determine whether maternal immunization affects the cytokine secretion pattern of splenocytes, either as a result of different relative lymphocyte numbers or as an indication of their activation, splenocytes were isolated from 18 female LDLR$^{-/-}$ mice that had been fed a cholesterol-enriched diet until age 5 months, and incubated with 30 µg OxLDL for 48 h at 37° C. under $CO_2$. Equal amounts of supernatant were pooled and 22 interleukins and chemokines quantitatively analyzed by Ray Biotech mouse cytokine array I (Table 2). Splenocytes from offspring of OxLDL-immunized mothers secreted significantly more IFNγ and RANTES (CCL5), and tended to secrete less TNFα, IL-2, IL-3, IL-4, IL-5, and IL-13. The increase in IFNγ, an important immunomodulator, is likely to reflect increased numbers of antigen-activated T cells, B cells, or NK cells. However, increased lymphocyte production of IFNγ cannot account for the diminished atherogenesis in offspring of OxLDL-immunized mothers, because IFNγ is proatherogenic. RANTES (CCL5) is a chemotactic T cell-generated chemokine that plays a prominent role in many acute viral infections, including HIV. Interestingly, it not only blocks HIV-1 replication in vitro, but has been proposed to protect the fetus from maternal HIV infection through alloantigen recognition in utero. It also seems to regulate host response to other intrauterine infections.

TABLE 2

Maternal immunization affects cytokine secretion of murine splenocytes.

| | OxLDL-immunized Mean ± SEM | Controls Mean ± SEM | P |
|---|---|---|---|
| GCSF | 991 ± 152 | 1,139 ± 29 | 0.39 |
| GM-CSF | 396 ± 68 | 625 ± 248 | 0.42 |
| IL-2 | 431 ± 75 | 730 ± 150 | 0.15 |
| IL-3 | 763 ± 133 | 1,111 ± 98 | 0.10 |
| IL-4 | 1,285 ± 116 | 1,623 ± 136 | 0.13 |
| IL-5 | 543 ± 140 | 852 ± 148 | 0.20 |
| IL-6 | 5,352 ± 839 | 3,053 ± 1080 | 0.17 |
| IL-9 | 207 ± 79 | 233 ± 80 | 0.83 |
| IL-10 | 2,571 ± 581 | 2,107 ± 248 | 0.50 |
| IL-12 p40p70 | 31,367 ± 1780 | 26,424 ± 3550 | 0.28 |
| IL-12p70 | 1,892 ± 97 | 1,684 ± 44 | 0.12 |
| IL-13 | 616 ± 69 | 875 ± 114 | 0.12 |
| IL-17 | 431 ± 100 | 327 ± 144 | 0.58 |
| IFNγ | 9,531 ± 3605 | 2,426 ± 872 | 0.01 |
| MCP-1 | 2,156 ± 730 | 1,160 ± 74 | 0.25 |
| MCP-5 | 525 ± 190 | 400 ± 154 | 0.64 |
| RANTES | 4,133 ± 201 | 3,160 ± 106 | 0.01 |
| SCF | 424 ± 92 | 282 ± 92 | 0.34 |
| sTNF RI | 827 ± 207 | 986 ± 214 | 0.62 |
| TNFα | 662 ± 154 | 1,185 ± 189 | 0.10 |
| Thrombopoietin | 1,386 ± 346 | 871 ± 20 | 0.21 |
| VEGF | 1,037 ± 391 | 524 ± 131 | 0.28 |

Splenocytes of 20 week old female offspring of OxLDL-immunized and control mothers were incubated with 30 mg/ml of OxLDL in RPMI 1640 medium + 10% FCS for 48 h at 37° C. under $CO_2$. Cytokines secreted were determined by BioRay mouse cytokine array in 3 pools of 3 mice each per group (duplicate measurements) and quantified by densitometry.

Figure 7:
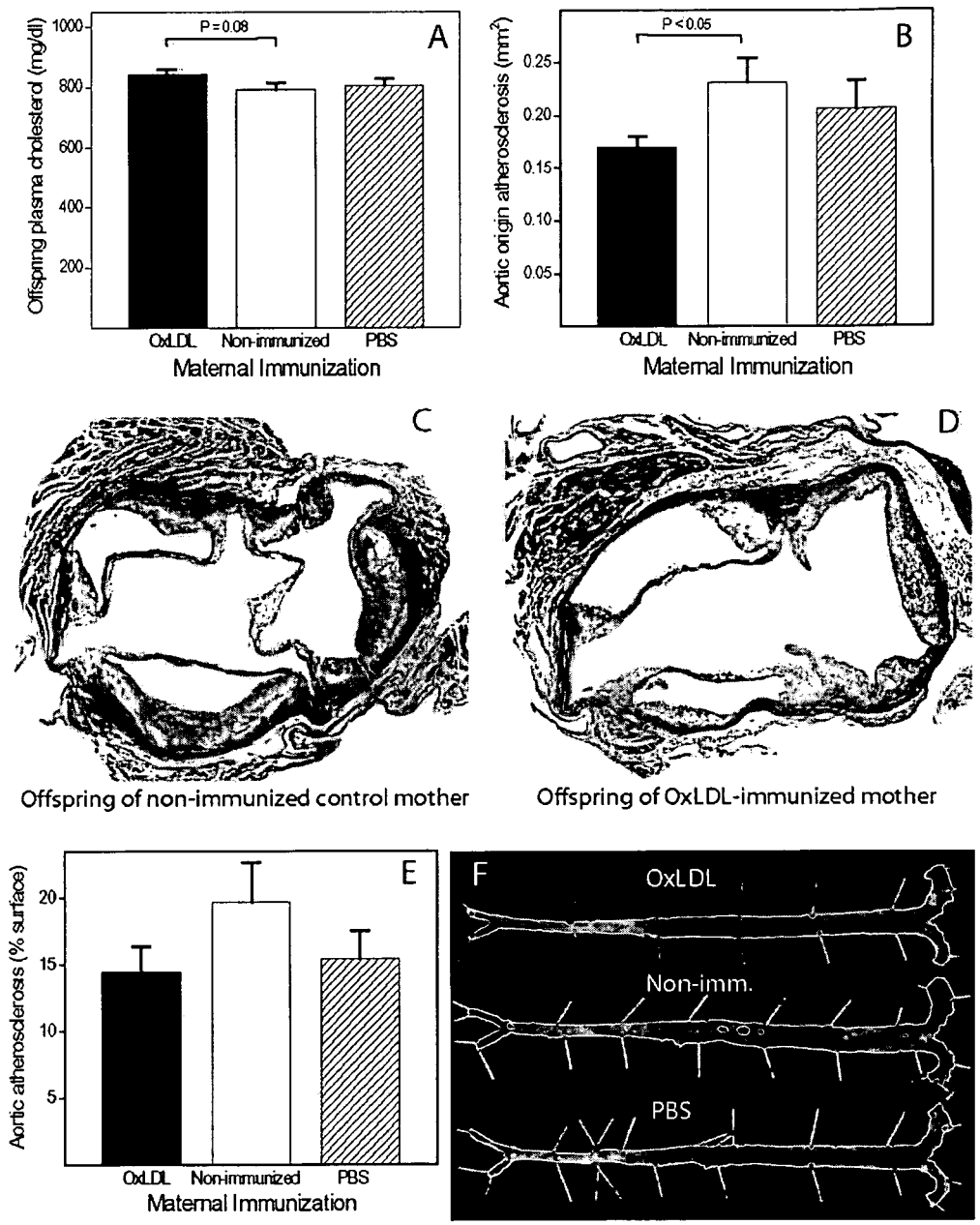
FIG. 7A-F shows that maternal immunization with OxLDL reduces atherogenesis in LDLR$^{-/-}$ mice. Female LDLR$^{-/-}$ mice immunized with homologous OxLDL or PBS FA, and nonimmunized controls, were fed regular chow during pregnancy. After weaning, offspring were fed cholesterol-enriched diet for 16 weeks (females, n=35) or 30 weeks (males, n=35). (A) Time-averaged total plasma cholesterol during the dietary intervention phase in female offspring. (B) Atherosclerosis in the aortic origin of female offspring at 20 weeks. (C and D) Representative trichrome stained cross-sections of the aortic origin showing atherosclerotic lesions underneath the aortic valve leaflets. Cumulative lesion areas of the sections shown are 0.28 and 0.17 mm$^2$, respectively. (E) Atherosclerosis in the entire aorta of male offspring at 34 weeks. (F) En face preparations of representative Sudan-stained aortas of male mice.

The time-averaged cholesterol level in all 20-week-old female offspring was about 800 mg/dL (FIG. 7A). Maternal immunization reduced cross-sectional lesion areas by 26%, compared with nonimmunized controls (P<0.05) (FIG. 7B-D). In 34-week-old male offspring, atherosclerosis of non-immunized controls covered 19.7% of the aortic surface, and maternal OxLDL immunization achieved an almost identical protective effect as in the aortic origin of 20-week-old females (FIGS. 6E, F). These results indicate that the antiatherogenic effect is not limited to a particular gender, anatomical site, stage of lesion, or parameter measured. Overall, the antiatherogenic effect of maternal immunization was less than that in rabbits, which may be because of the moderate maternal hypercholesterolemia and a lesser impact of immune mechanisms in offspring exposed to much greater postnatal hypercholesterolemia. The effects of maternal immunization on postnatal humoral immunity and atherosclerosis thus appear to be species-independent.

Figure 8:
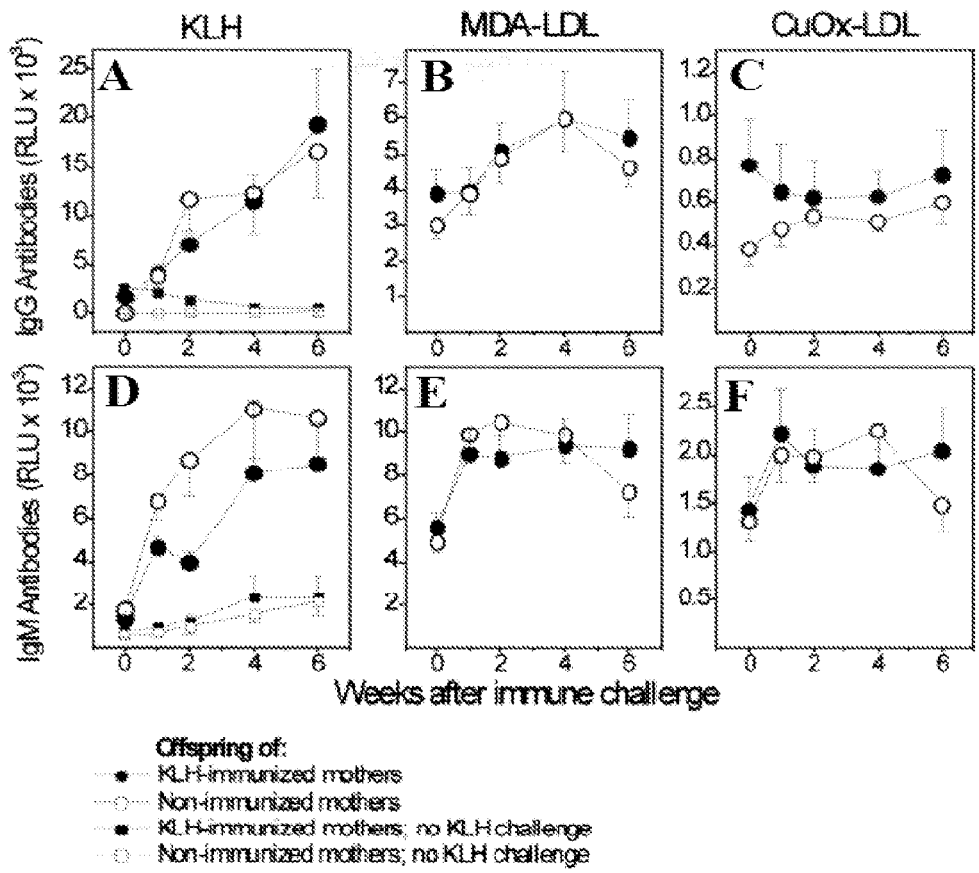
FIG. 8A-F shows maternal immunization with KLH does not influence postnatal immune responses to KLH in mice. Offspring of LDLR$^{-/-}$ mothers immunized with KLH without adjuvant (n=11) and non-immunized controls (n=12) on regular chow received a single subcutaneous injection of KLH at age 6 weeks. IgG and IgM antibodies to KLH and OxLDL were followed for 6 weeks. Three offspring of each maternal group that were not subjected to KLH challenge are included as additional controls. Therefore, results are reported as antibody concentration. (A) Circulating IgG antibodies to KLH. (B and C) IgG to MDA-LDL and CuOx-LDL, respectively. (D) IgM antibodies to KLH. (E and F) IgM to MDA-LDL and CuOx-LDL, respectively, in the absence of an Ox LDL challenge, antibodies to Ox LDL did not increase over time.

The increased antibody binding to native LDL in atherosclerotic offspring of OxLDL-immunized mice and immune-challenged naïve NZW rabbits, and the partial antiatherogenic effect of maternal immunization with PBS+FA suggest that in utero programming is not specific for, or limited to, OxLDL. To assess whether the presence of the antigen in arterial or other tissues of fetuses and offspring is a prerequisite of immune programming, analogous maternal immunization was carried out with KLH, a T cell-dependent antigen that does not naturally occur in mammals. Six weeks old offspring of KLH-immunized and non-immunized controls (n=11, each) were subjected to a single injection of KLH (without adjuvants), and antibodies to KLH and OxLDL followed for 6 weeks. In contrast to the analogous experiment in NZW rabbits, which yielded significantly greater responses to OxLDL, but not KLH, in offspring of OxLDL-immunized mothers, maternal immunization with KLH did not increase IgG or IgM responses to KLH (FIG. 8). Thus, the programming of postnatal immune responses either depends on the presence of the antigen in fetuses or offspring or is limited to T cell independent antigens. Results of KLH immunization also provide additional evidence that the results in challenged offspring of OxLDL-immunized rabbits and mice were not due to persistence of maternal IgG.

The data presented here support two unexpected conclusions. First, that maternal immunization with antigens commonly found in atherosclerotic lesions markedly reduces the susceptibility to atherosclerosis in their offspring. Second, that maternal immunization induces persistent changes in B and T cell-dependent immune responses in their offspring that are not attributable to known mechanisms, such as transplacental passage of immunoglobulins or coating of intestinal surfaces by maternal immunoglobulins during lactation. Thus, adaptive immune responses induced by maternal immunization with antigens prevalent in humans, such as OxLDL, lead to fetal immune programming, that may influence adult diseases. The results show that neonatal protection is not limited to passive immune protection, that adult immune responses are influenced by fetal programming, that maternal immune memory influences adult disease (e.g., atherosclerosis), and that both fetal programming and postnatal disease can be influenced by active immune modulation of the mother.

Although substantial epidemiological evidence supports the concept that developmental programming influences disease manifestation and severity later in life, relatively little is known about the underlying mechanisms. However, rabbit and mouse models have confirmed the association between maternal hypercholesterolemia and increased fetal and postnatal atherogenesis observed in humans. Experiments in these models have also established the causal role of increased lipid peroxidation and the protective effect of cholesterol-lowering and antioxidant interventions in mothers.

Given the influence of maternal cholesterol, which was also confirmed by the data presented herein (FIG. 1), one would expect maternal immunization to affect postnatal disease (e.g., atherosclerosis) by reducing fetal cholesterol exposure, e.g. by the formation of immune complexes between induced antibodies and LDL particles bearing a limited number of oxidation-specific epitopes and their subsequent removal from the circulation. The fact that the relative antiatherogenic effect was greatest in offspring of extensively hypercholesterolemic rabbits suggests that this was indeed a protective mechanism. However, offspring of extensively and marginally hypercholesterolemic NZW mothers exposed to the same dietary cholesterol levels developed almost identical lesions. Thus, the antiatherogenic mechanism was not limited to a decrease in fetal cholesterol exposure. In view of the well documented antiatherogenic effects of OxLDL immunization exerted in immunized experimental subjects, it can be assumed that some of the immune responses primed in offspring contributed to the postnatal antiatherogenic effect by similar mechanisms.

The observation of persistently increased IgM immune complexes in offspring of OxLDL-immunized mothers rabbit and mouse mothers subjected to postnatal hypercholesterolemia (FIGS. 2A and 4D), the increase in IgM antibodies to various oxidation-specific epitopes in the same mice (FIGS. 4B, C), and the markedly increased humoral immune responses to OxLDL, but not KLH, in naïve normocholesterolemic rabbit offspring after a single immune challenge with both antigens (FIGS. 3E-L) provide ample evidence that fetal immune programming influences IgM immune responses later in life. The simultaneous increase of IgG titers after the OxLDL challenge (FIG. 3B-D) is indicative of a secondary response, and is also important from a practical point, because it suggests that maternal immunization is also capable of inducing IgG response, given a proper postnatal boost. While offspring IgG levels shortly after birth (e.g., in 4 week old mice) clearly reflect active transplacental transport and maternal IgG levels (FIG. 4A), this cannot account for later differences, e.g., in immune-challenged rabbits (FIG. 3), or differences in IgM antibodies, which do not cross the placental barrier and are not taken up into the blood stream during lactation. Greater numbers of IgM-secreting splenic cells in offspring of OxLDL-immunized mothers at the end of the challenge in rabbit (FIG. 3M) and in hypercholesterolemic mice (FIG. 4F) are also consistent with fetal immune programming, but not with placental or neonatal antibody transfer.

In the absence of exogenous antigen challenge, humoral immune response in mice were extensive, but in rabbits, only IgM immune complexes were increased, whereas no corresponding increases in IgM antibodies to extensively MDA-modified or copper-oxidized LDL epitopes were seen (FIG. 2). Two possible explanations may account for this. First, it is possible that increases in the specific IgM binding to circulating LDL particles were more than compensated for by the formation and removal from plasma of immune complexes. Second, it is possible that the increase in IgM-LDL immune complexes was due to a population(s) of IgM specific for unknown epitopes not prevalent in the two models of OxLDL tested.

The protective role of maternal adaptive immunity for their offspring is well established in humans and animals. In humans, this protection has been attributed almost exclusively to maternal IgG carried across the placenta, whereas in many animals additional protection is conveyed by maternal immunoglobulins coating intestinal enterocytes during lactation. The passive immune protection by maternal IgG does not extend much in time, but gives rise to increased adaptive immune responses and better long-term immunity in children boosted by early contact with exogenous antigen. The increase of IgM in offspring of OxLDL-immunized mothers cannot be attributed to placental passage. However, humoral immune responses in offspring and the antiatherogenic effect may have been enhanced by an analogous mechanism, because in both animal models and humans consuming Western diets, continuous formation of antigen in the arterial wall can be assumed to occur.

It is noteworthy that fetal development of immune cells begins very early, and that hematopoietic cells in the mouse are already present towards the end of the first trimester, even though it remains unclear at what stage these progenitor cells differentiate into lymphocytes. Although adaptive immune defenses are generally thought to become fully functional only after birth, in humans mature CD4 positive T cells already occur in the 17th week of gestation, and various forms of OxLDL that could induce antigen-specific T cell responses are abundant in both plasma and arterial tissues of human fetuses by the end of the second trimester. Placental passage of maternal oxidized fatty acids and fetal lipid peroxidation may both contribute to fetal antigens. It is possible that maternal immunization modulates the amount of antigen in the fetus, and thus fetal B and T cell differentiation, by affecting the maternal and fetal availability of antigen. Postnatal immune memory could also be influenced by the amount of OxLDL persisting in lymphoid tissue.

Interactions between innate and adaptive immunity may also be relevant. It is increasingly recognized that the differentiation and proliferation of B-1 cells secreting "natural" IgM antibodies is not limited to a brief postnatal period, but may already begin during fetal development, and that Th-independent antibody responses may in fact be influenced by antigen exposure. The observation that EO6/T15 idiotype antibodies are increased in atherosclerotic apoE-deficient mice also suggests that antigens formed or accumulated in atherosclerotic lesions, such as OxLDL, may not just stimulate memory T and B cell, but also some B-1 cells. Whether such antigen-dependent differentiation already occurs during fetal development and to what extent the increased IgM responses observed represent innate, B-1 cell-derived IgM remains to be determined. Although IgM binding to PC (an antigen recognized by T15/EO5 antibodies) was increased in mice (FIG. 4C), the increase of T15/EO5 IgM itself did not reach significance, and FACS analysis of peritoneal B-1 cells in naïve mice after 2 weeks on hypercholesterolemic diet did not indicate quantitative difference in B-1 cells.

The notion that B- and T-cell dependent IgM and IgG responses are programmed in utero by maternal adaptive immunity, apparently independently of the prevalence of antigen (i.e., maternal or fetal OxLDL that correlates with the degree of hypercholesterolemia during pregnancy) is contrary to the prevailing notion that modulation of adaptive (and innate) immune responses can only be achieved once immune cells have matured. The findings presented herein are consistent, however, with recent suggestions that the in utero environment also plays an important role in the development of allergy later in life. In fact, allergen-specific T-cells are already present in most newborns and seem to be of fetal origin. Evidence for an effect of prenatal immunization and for an involvement of maternal T and B cells in shaping allergic responses of adult offspring has also recently been reported.

Experimental design of studies investigating the effect of immune modulation on insulin resistance. Two complementary experiments were performed. The first was designed to assess the effect of maternal immunization on developmental programming. Female LDLR$^{-/-}$ mice (bred-back into C57BL\6 for at least 10 generations), age 6-8 weeks, were immunized with homologous nLDL. The latter was isolated by density gradient ultracentrifugation from LDLR$^{-/-}$ mice fed a 1.25% cholesterol diet (Harlan Teklad TD96121) for about 4 weeks, and stored without antioxidant protection at 3° C. until use. The rationale for this antigen was that offspring of rabbits and mice immunized with OxLDL showed greater binding of circulating IgM and IgG antibodies to nLDL than OxLDL. Although nLDL contains a small number of the same oxidation-specific epitopes as OxLDL, it is likely to contain more epitopes of early reaction products between lipid peroxidation products and (apolipo)proteins or phospholipids, which are lost during more extensive oxidation (or glycation). As nLDL is not recognized and removed from the circulation by hepatic scavenger receptors, such epitopes—and antibodies directed against them—may be of biological relevance. In fact, immunization of adult rabbits and mice with native LDL has previously been shown to reduce atherogenesis, even though titers to conventional oxidation-specific epitopes rose only insignificantly. After verifying a positive immune response, mothers were continued on regular murine chow and mated. Following weaning at 4 weeks, offspring of all maternal groups were fed a regular chow supplemented with 0.5% cholesterol (Harlan Tekland TD 07234; mixed with 0.25% cholesterol diet TD 99260 if the cholesterol of individual mice exceeded 900 mg/dl) for 16 weeks (females) or 30 weeks (males), at which time atherosclerosis was determined in the aortic origin. In addition, a single OGTT was performed in offspring, about a week before sacrifice. Male and female offspring were treated as separate groups.

The second experiment focused on the effects of immunization with either nLDL or OxLDL on insulin resistance (IR) in the immunized animals themselves. As several OGGTs over time had to be performed, which would have constituted a confounding element in the offspring study, these experiments were performed in separate groups of male or female mice fed one of three different diets for up to a year. Diets were: 1) regular chow; 2) regular chow supplemented with 0.5% cholesterol to yield moderate hypercholesterolemia and atherogenesis; or 3) a low-fat, high-carbohydrate diet intended to yield greater obesity and IR, termed "60% Sucrose" diet in the following (Harlan Teklad TD 05516, containing 50% (wt/wt) sucrose, 20.7% casein, 7.696% cellulose, 5% lard, 5% mineral mix, 1% vitamin mix, 0.3% DL-methionine, 0.3% choline bitartrate, and 0.004% zinc carbonate).

Immunization. Mice were immunized with homologous nLDL (isolated by density gradient ultracentrifugation and stored without antioxidant protection at 3° C. until use), or OxLDL. To obtain a broad spectrum of oxidation-specific epitopes, OxLDL consisted of an equal mixture of malondialdehyde-modified and copper-oxidized LDL. LDL was tested for endotoxin levels by chromogenic *Limulus amoebocyte* assay (QCL-1000; BioWhittaker) and contained less than 2 ng lipopolysaccharides/mg protein. The primary immunization consisted of inguinal intradermal injection of the antigen (60 µg protein/kg body weight) emulsified with an equal amount of complete Freund's Adjuvant (FA) (Sigma F-5881). Two boosts consisted of subcutaneous injection of 30 µg antigen in incomplete FA (Sigma F-5506). Because previous work had indicated weak but consistent protective effects of FA, non-immunized mice were used as controls, in addition to PBS+FA immunized ones. After the second boost, immune response were ascertained by ELISA.

Oral glucose tolerance test. Blood samples (20-25 µl) were collected from the retro-orbital plexus of isoflorane-anesthetized, fasted mice prior to glucose gavage and 15, 30, 60, 90, and 120 min thereafter. Gavage consisted of intragastric administration of 1.5 ml/kg body weight of a sterile 10% glucose solution via a stainless steel animal feeding needle. Glucose was determined by glucose test strips (Devine Medical Supplies) and QID glucometer (MediSense), and plasma insulin levels by Mercodia Ultrasensitive Mouse Insulin Kits (American Laboratory Products).

Figure 9:
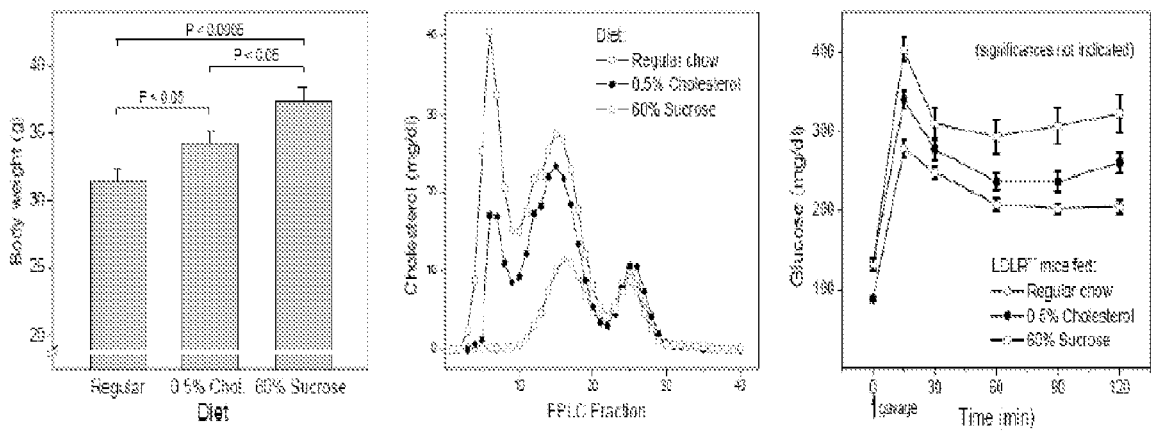
FIG. 9 shows the effect of diets on body weight (left), lipoprotein profile (middle) and glucose responses in an oral glucose tolerance test (OGTT) (right). Data represent male LDLR$^{-/-}$ mice fed regular chow, regular chow supplemented with 0.5% cholesterol, or a 60% sucrose diet for 4 months. n=9, 11, and 11 in the control, 0.5% cholesterol, and 60% glucose groups, respectively; FPLC analysis of lipoproteins was performed on pooled plasma samples.

In order to develop a model in which the mechanisms of gestational IR on in utero programming and the effects of maternal immunization on offspring immune responses can be investigated, an experiment was performed in LDLR$^{-/-}$ mice fed various diets. This was guided by a number of previous observation. Specifically, diabetic conditions in mice can easily be induced by streptozotocin, but diabetic mice breed very poorly. Multiple injections of low-dose streptozotocin beginning at the fifth day of gestation overcome this problem, but result in an acute inflammatory condition during pregnancy that is unlikely to be representative of human gestational diabetes and would be unsuitable to study immune programming by preexisting maternal adaptive immunity. Standard high-fat, 1.25% cholesterol diets routinely used to induce atherosclerosis in LDLR$^{-/-}$ mice not only cause extensive hypercholesterolemia, but also obesity and IR. However, such diets also severely reduce pregnancy outcome, whereas short term feeding of regular chow supplemented with cholesterol does not result in significant IR, at least within a few months. A custom high carbohydrate diet (60% sucrose) was compared to standard chow and 0.5% cholesterol diet in male mice. As shown in FIG. 9, the 60% sucrose diet resulted in significantly greater gain in body weight and affected lipoprotein profiles and glucose responses more than the 0.5% cholesterol diet. Cholesterol levels increased over time in all groups, reaching a plateau after about 5 months (346±13 mg/dl in the control group, 889±25 mg/dl in the 0.5% cholesterol group and 1245±61 mg/dl in the 60% sucrose group).

Figure 10:
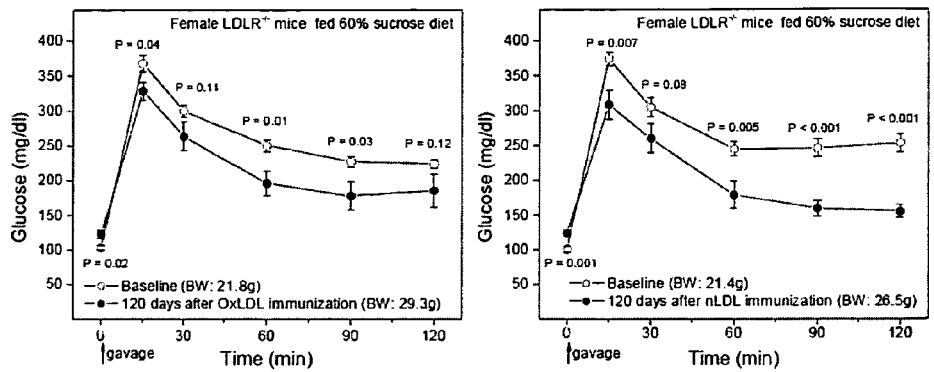
FIG. 10 shows that immunization with nLDL (left) or OxLDL (right) improves glucose responses in mice fed an obesogenic diet. Female mice were immunized 4 days after a baseline OGTT. Three weeks later, i.e. one week after the first boost, mice were started on the 60% sucrose diet, and a second OGGT was performed 120 days later. The data show a protective effect of immunization. n=13 and 12 in the OxLDL and nLDL groups, respectively.

Female mice fed the 60% sucrose diet were therefore used for an initial assessment of the effect of maternal immunization prior to diet-induced IR and pregnancy. As shown in FIG. 10, glucose response were significantly improved in an OGTT performed after 120 days on the diet, compared to the pre-diet OGTT, whereas in non-immunized male controls the same diet had impaired glucose responses (FIG. 9). Total cholesterol (TC) levels and body weights (BW) tended to be slightly higher in the OxLDL group, compared to the nLDL group, but neither difference was significant (762±38 vs. 650±51 mg/dl TC and 29.3±0.7 vs. 26.5±0.7 g BW). Although FIG. 10 represents a longitudinal comparison between OGTTs performed at different time points and lacks non-immunized female controls, results suggested a protective effect of immunization on IR. Given the nature of the immunogens, which are not specific to IR or diabetes and were used primarily because of their established (OxLDL) and hypothetical (nLDL) effect on oxidation-sensitive in utero programming, the degree of protection apparently offered to the immunized animals themselves was not anticipated, and raised the question whether immunotherapy protects against or delays the onset of IR, in general.

Figure 11:
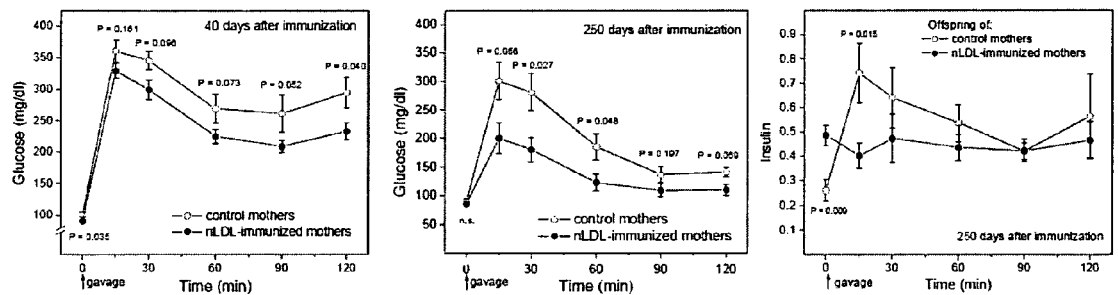
FIG. 11 shows immunization with native LDL improves glucose responses even in non-insulin-resistant LDLR$^{-/-}$ mice fed regular chow. Prospective mothers of the in utero programming study were immunized with native LDL and a first OGGT performed 40 days after the primary immunization (left), a second after 250 days (middle). Despite the greater hyperglycemic response in the non-immunized control group its corresponding insulin levels were significantly higher (right).

Results of the in utero programming experiment—initially designed to evaluate the effect of maternal nLDL immunization in offspring—established that immunization with this antigen not only reduces or delays IR in mice fed obesogenic diets, but also improves glucose responses in non-insulin resistant LDLR$^{-/-}$ mice fed regular chow (FIG. 11). OGGTs performed 40 and 250 days after the primary immunization showed markedly attenuated hyperglycemic responses in the immunized group, indicating that the protective effect persists over a long time, at least in the absence of conditions strongly promoting IR. Insulin measurements (right panel) were indicative of greater insulin sensitivity in the immunized group, because the control group developed higher glucose levels after gavage despite greater insulin release. Again, body weights and cholesterol levels were similar in both groups.

Figure 12:
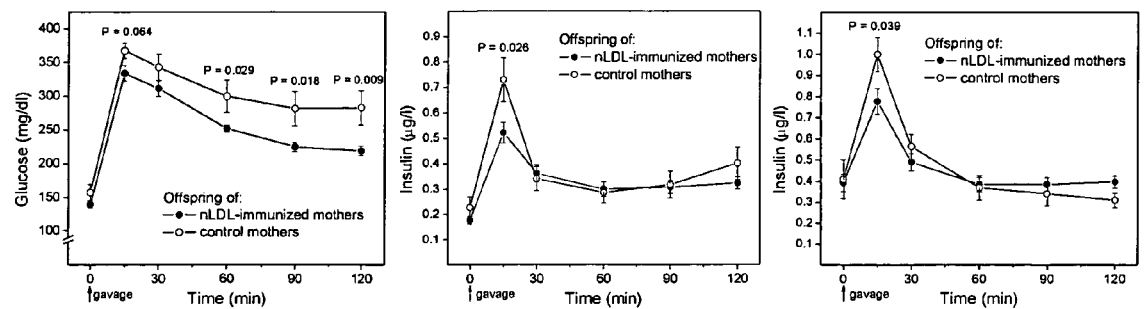
FIG. 12 shows that maternal immunization with nLDL protects against IR. Male offspring of nLDL-immunized mothers and controls (n=15 and n=11, respectively) were weaned at age 4 weeks and fed a 0.5% cholesterol diet for 30 weeks, at which time atherosclerosis was determined. The OGTT depicted was carried out one week earlier. Male offspring of nLDL-immunized mothers showed lesser increases in glucose and faster return to normal than controls (left), even though the latter responded to the glucose challenge with a greater insulin peak (middle). Female offspring fed the same diet for only 16 weeks (n=25 and n=12 in the nLDL and control groups, respectively) did not differ in their glucose responses, but insulin peaks were also greater in controls (right).

Offspring of non-immunized and nLDL-immunized euglycemic mothers were fed the 0.5% cholesterol diet for 16 or 30 weeks, i.e. until age 20 (females) or 34 weeks (males). Using the current and past control groups as internal standard allowed us to compare atherosclerosis in offspring of nLDL-immunized mothers in the present experiment to those of OxLDL-immunized mothers in the previous one. IR in offspring was assessed by a single OGTT, a week before sacrifice. As shown in FIG. 12, maternal nLDL immunization significantly reduced the hyperglycemic response to oral glucose challenge in male offspring (left), even though offspring of non-immunized controls responded with a significantly greater peak insulin release (middle). A protective effect was also evident in female offspring fed the same diet for only 16 weeks. Although in this case non-immunized controls still showed normal glucose responses, they required greater insulin release to do so (right). Time-averaged cholesterol levels were similar in immunized and control females ($713\pm18$ vs. $760\pm25$ mg/dl; n=25 and 12, respectively) and males ($792\pm27$ vs. $769\pm4$ mg/dl; n=15 and 10, respectively). Body weights in females were also similar ($23.0\pm0.4$ vs. $22.8\pm0.3$ g), whereas nLDL-immunized males gained slightly weight than controls ($33.1\pm0.7$ vs. $37.8\pm1.8$ g; $P<0.02$). The older males of both groups were obviously far more obese than the younger females.

Figure 13:
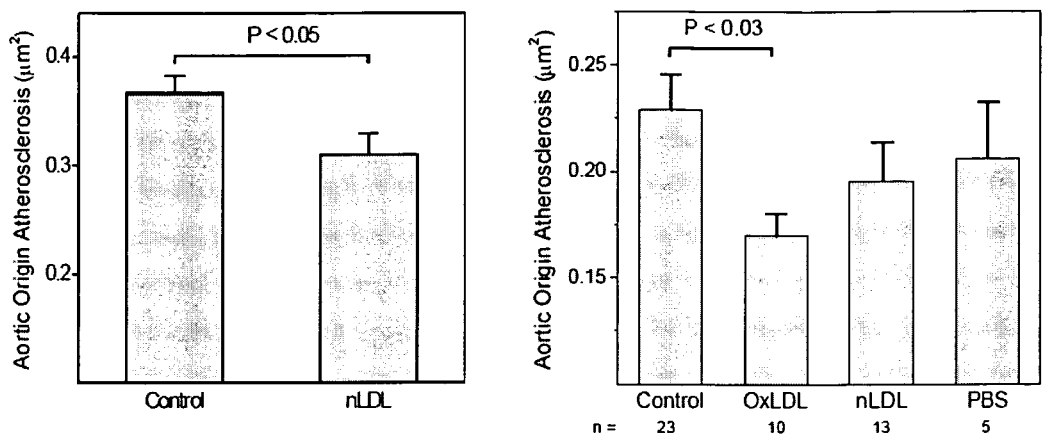
FIG. 13 shows maternal immunization with nLDL is less efficient in reducing offspring atherosclerosis than immunization with OxLDL. Male offspring of nLDL-immunized mothers showed a 15% reduction of atherosclerosis in the aortic origin after 30 weeks on 0.5% cholesterol diet (0.37±0.016 vs. 0.21±0.020 mm$^2$/section, P<0.05) (left), but a similar 15% protection of female offspring after 16 weeks on the same diet did not reach significance (P=0.20), in contrast to the 26% reduction observed under identical conditions in offspring of OxLDL-immunized mothers (right).

Maternal immunization with nLDL was less efficient in reducing offspring atherosclerosis than immunization with OxLDL (FIG. 13). Although male offspring of nLDL-immunized mothers showed a 15% reduction of atherosclerosis in the aortic origin after 30 weeks on 0.5% cholesterol diet ($0.37\pm0.016$ vs. $0.21\pm0.020$ mm$^2$/section, $P<0.05$), a similar 15% reduction in female offspring after 16 weeks did not reach significance ($P=0.20$), in contrast to the 26% reduction previously observed under identical conditions in offspring of OxLDL-immunized mothers.

Figure 14:
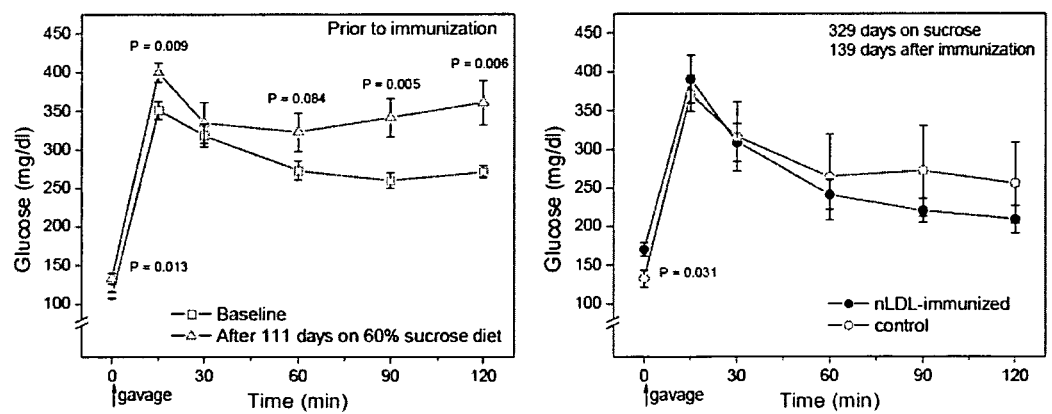
FIG. 14 shows that immunization with nLDL conveys protection even to animals who have already developed insulin resistance. 14 male LDLR$^{-/-}$ mice were fed the 60% Sucrose diet for 190 days to induce IR (left). 9 mice were then immunized, the rest served as control. Glucose responses in an OGTT were determined 20 weeks (139 days) after the primary immunization, i.e. after 339 days on diet (right). A trend towards better protection is apparent.

The remarkable improvement of glucose responses in nLDL-immunized mice raises the question of whether this protective effect is only directed against mechanisms contributing to the onset of IR, or whether immunization also attenuates the effects of established IR. To address this, 14 male LDLR$^{-/-}$ mice were fed the 60% sucrose diet for 190 days to induce IR (FIG. 14, left). Of these, 9 were then immunized, the rest served as control. 139 days later, immunized mice showed only a trend towards better glucose responses (FIG. 14, right).

Results indicated that prior immunization with either OxLDL or nLDL markedly improves glucose responses in euglycemic LDLR$^{-/-}$ mice fed regular chow and protects against the onset of IR induced by obesogenic diets, such as the 60% sucrose diet. These findings suggest that immunotherapy may prevent or delay the onset of IR. In addition, offspring of nLDL-immunized mothers fed regular chow during pregnancy also showed better glucose responses, and required less insulin to do so, after prolonged exposure to cholesterol-rich diet, indicating that modulation of maternal immunity not only affects developmental programming of atherosclerosis, but also postnatal glucose responses.

Neither OxLDL nor nLDL are specific for IR or diabetes. Both immunogens were chosen not because a strong effect on glucose metabolism was expected, but because of their effect on atherosclerosis, which in humans is markedly enhanced in diabetic subjects. Immunization with these antigens triggers extensive humoral and cellular immune responses, including the formation of IgG and IgM antibodies to various oxidation-specific epitopes that bind to oxidatively modified lipoproteins, proteins and phospholipids. Elimination of the resulting immune complexes with LDL from the circulation may be one mechanism contributing to the antiatherogenic effect of immunization. It is therefore tempting to assume that the protection against the development of IR is also due to interference with oxidation-sensitive mechanisms. Surprisingly little is known about the mechanisms responsible for IR. Attention has focused on genetic defects in insulin receptors, insulin receptor substrate proteins, and their downstream signaling, as well as on factors that impair insulin sensitivity and are typically increased in obesity, such as non-esterified fatty acids.

Another key feature of obesity is increased inflammation. Macrophages in adipose tissues are a prominent source of inflammatory cytokines, which in turn promote leukocyte activation and formation of reactive oxygen species. Oxidative stress has therefore been proposed to enhance IR and type 2 diabetes, but antioxidant interventions in insulin resistant or diabetic patients and animal models have not established its causal role in the progression from IR to diabetes, much less in the onset of IR. Several modulators of insulin sensitivity are regulated by oxidation-sensitive pathways, such as the NFkB, PPAR, and apoptotic pathways. However, increased lipid peroxidation may both promote IR, e.g. by increasing expression of TNF$\alpha$ activating c-Jun kinase and IkB kinase-$\beta$, and increase insulin sensitivity, e.g. by downregulating proinflammatory cytokines. Inducible nitric oxide synthase (iNOS), another oxidation sensitive factor, also affects IR.

The beneficial effect of OxLDL and nLDL immunization in mice fed carbohydrate and cholesterol-enriched diets supports a pathogenic role of oxidative stress in the onset of IR. Even the improved glucose responses in mice who were fed regular chow and were clearly neither obese nor insulin resistant is consistent with this assumption, because LDLR$^{-/-}$ mice are spontaneously hypercholesterolemic. On the other hand, oxidation-independent consequences of maternal immunization, such as altered T cell cytokines, may also influence insulin secretion and sensitivity.

With regard to developmental programming of atherosclerosis, the present results suggest that OxLDL is a far more effective immunogen than nLDL, even though offspring antibodies enhanced by OxLDL-induced fetal programming had previously shown better binding to nLDL than to the maternal immunogen. This may indicate that immune responses to epitopes of more extensively oxidized LDL offer better protection, but it is also possible that nLDL was merely a weaker immunogen, e.g. because the number of oxidative neoepitopes per particle is lower than on OxLDL.

A result of the disclosure was the consistent improvement of glucose responses and the apparent long-lasting protection against the onset of IR conveyed by the immunization. Whether the same intervention also protects subjects in which IR is already established remains to be determined, but preliminary experiments in a small number of animals suggest that the protection is much weaker. Nevertheless, immunoprevention of IR by itself would be a worthwhile goal.

A number of embodiments have been described. Nevertheless, it will be understood that various modifications may be made without departing from the spirit and scope of the description. Accordingly, other embodiments are within the scope of the following claims.

What is claimed is:

1. A method of immunization, comprising administering an antigen containing epitopes formed by oxidation or glycation of a phospholipid to a pregnant subject or soon to be pregnant subject, wherein the immune response in the pregnant subject or soon to be pregnant subject induces non-passive immune programming in the resulting offspring to the antigen, so that the resulting offspring produces IgG and IgM, or IgM antibodies to the antigen, wherein the antigen is selected from LDL, HDL, VLDL, IDL and LP(a), peptides of apolipoprotein B-100 or other apolipoproteins, or phospholipid components of lipoproteins.

2. A method of fetal immune programming comprising administering an antigen containing epitopes formed by oxidation or glycation of a phospholipid to a pregnant female subject or soon to be pregnant female subject, wherein the immune response in the female subject induces non-passive fetal immune programming during pregnancy so that the resulting fetus produces IgG and IgM, or IgM antibodies to the antigen, wherein the antigen is selected from LDL, HDL, VLDL, IDL and LP(a), peptides of apolipoprotein B-100 or other apolipoproteins, or phospholipid components of lipoproteins.

3. The method of claim 1 or 2, wherein said method of administration comprises oral, intravenous, parenteral, transdermal, subcutaneous, intravaginal, intraperitoneal, intranasal, mucosal, sublingual, topical or rectal administration, or any combination thereof.

4. The method of claim 1 or 2, wherein the antigen is selected from the group consisting of an antigen that induces autoimmune disease, and an autologous antigen.

5. The method of claim 1 or 2, wherein the antigen comprises a neoepitope formed by oxidation, glycation, or a combination thereof.

6. The method of claim 4, wherein the disease or disorder comprises atherosclerosis, obesity, insulin resistance, the metabolic syndrome, non-insulin dependent diabetes mellitus (NIDDM), and insulin dependent diabetes mellitus (IDDM).

7. The method of claim 4, wherein the autoimmune disorder is IDDM.

8. A method for treating or reducing the risk of developing an autoimmune disorder comprising administering to a pregnant maternal subject or soon to be pregnant maternal subject, an immunomodulatory effective amount of at least one epitope from a self-antigen comprising epitopes formed by oxidation or glycation of a phospholipid in a pharmaceutically acceptable carrier, wherein the epitope induces a non-passive immune response in the maternal subject and wherein the maternal subject's immune response provides immune programming in a fetus, so that the fetus produces IgG and IgM, or IgM antibodies to at least one epitope of the self-antigen, wherein the antigen is selected from LDL, HDL, VLDL, IDL and LP(a), Peptides of apolipoprotein B-100 or other apolipoproteins, or phospholipid components of lipoproteins.

9. The method of claim 8, wherein the subject is a human.

10. The method of claim 8, wherein the autoimmune disorder is diabetes.

11. The method of claim 8, wherein the epitope comprises an antigen selected from the group consisting of an antigen that induces autoimmune disease, and an autologous antigen.

12. The method of claim 8, wherein the antigen comprises an oxidative neoepitope.

13. The method of claim 11, wherein the disease or disorder comprises atherosclerosis, obesity, insulin resistance, the metabolic syndrome, non insulin dependent diabetes mellitus (NIDDM), and insulin dependent diabetes mellitus (IDDM).

14. A method of inducing protective immunity in a subject comprising administering an antigen containing epitopes formed by oxidation or glycation of a phospholipid to a female subject just prior to or during pregnancy so that upon the birth the subject comprises a programmed immunity to the antigen, by producing IgG and IgM, or IgM antibodies to the antigen, wherein the antigen is selected from LDL, HDL, VLDL, IDL and LP(a), peptides of apolipoprotein B-100 or other apolipoproteins, or phospholipid components of lipoproteins.

15. The method of claim 14, further comprising boosting the programmed immunity of the subject after birth, comprising administering the antigen to the neonate subject.

16. The method of claim 1, comprising administering an antigen containing epitopes formed by oxidation or glycation of a phospholipid to a pregnant subject, wherein the immune response in the pregnant subject induces non-passive immune programming in the resulting offspring to the antigen, so that the resulting offspring produces IgG and IgM, or IgM antibodies to the antigen.

17. The method of claim 8, comprising administering to a maternal subject during pregnancy, an immunomodulatory effective amount of at least one epitope from a self-antigen comprising epitopes formed by oxidation or glycation of a phospholipid in a pharmaceutically acceptable carrier, wherein the epitope induces a non-passive immune response in the maternal subject and wherein the maternal subject's immune response provides immune programming in a fetus, so that the fetus produces IgG and IgM, or IgM antibodies to at least one epitope of the self-antigen.

18. The method of claim 14, comprising administering an antigen containing epitopes formed by oxidation and glycation of a phospholipid to a female subject during pregnancy so that upon birth of the subject, the subject has programmed immunity to the antigen, by producing IgG and IgM, or IgM antibodies to the antigen.

* * * * *